US006375980B1

(12) United States Patent
Densmore, Jr. et al.

(10) Patent No.: US 6,375,980 B1
(45) **Date of Patent: *Apr. 23, 2002**

(54) STABILIZATION OF LIPID:DNA FORMULATIONS DURING NEBULIZATION

(75) Inventors: Charles L. Densmore, Jr., The Woodlands; J. Vernon Knight, Houston; J. Clifford Waldrep, The Woodlands; Berma M. Kinsey, Houston, all of TX (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/356,635

(22) Filed: Jul. 19, 1999

Related U.S. Application Data

(63) Continuation-in-part of application No. 09/227,648, filed on Jan. 8, 1999, now Pat. No. 6,106,859.

(60) Provisional application No. 60/071,052, filed on Jan. 8, 1998.

(51) Int. Cl.[7] ........................ A16K 9/127; A16K 51/00; C12N 15/88

(52) U.S. Cl. ........................ 424/450; 424/43; 424/1.21; 435/458

(58) Field of Search ................................ 424/1.21, 450, 424/43; 435/458

(56) References Cited

U.S. PATENT DOCUMENTS

| | | | | | |
|---|---|---|---|---|---|
| 5,077,211 | A | * | 12/1991 | Yaroush | 435/193 |
| 5,292,746 | A | * | 3/1994 | Carr et al. | 514/278 |
| 5,469,854 | A | * | 11/1995 | Unger et al. | 600/458 |
| 5,641,662 | A | * | 6/1997 | Debs et al. | 435/458 |
| 6,106,859 | A | * | 8/2000 | Densmore et al. | 424/450 |

FOREIGN PATENT DOCUMENTS

| | | | | |
|---|---|---|---|---|
| EP | 0 211 647 | * | 2/1987 | 424/450 |

OTHER PUBLICATIONS

Vigneron et al (Proc. Nat. Acad. Sci. USA 93:9682–9686, See entire document, especially abstract; p. 9683, col. 1, lines 1–5 of first full paragraph; p. 9684, col. 1, lines 1–3 of second full paragraph; p. 9685, col. 2, lines 3–6, and Figure, Sep. 1996.*

* cited by examiner

*Primary Examiner*—Robert A. Schwartzman
*Assistant Examiner*—Richard Schnizer
(74) *Attorney, Agent, or Firm*—Benjamin Aaron Adler

(57) ABSTRACT

The present invention provides a liposomal aerosol composition, comprising a pharmaceutical compound, a cationic lipid, a neutral co-lipid; and tryptone. Also provided is a nebulized cationic lipid: neutral co-lipid: DNA suspension useful for lipid-DNA transfections, wherein the cationic lipid is bis(guanidinium)-tren-cholesterol and the neutral co-lipid is dioleoylphosphatidylethanolamine (DOPE).

9 Claims, 22 Drawing Sheets

STABILIZATION OF LIPID:DNA FORMULATIONS DURING NEBULIZATION

CROSS-REFERENCE TO RELATED APPLICATION

This patent application is a continuation-in-part of U.S. application Ser. No. 09/227,648, filed Jan. 8, 1999, now U.S. Pat. No. 6,106,859, issued Aug. 22, 2000. This application also claims benefit of U.S. Provisional Application No. 60/071,052 field Jan. 8, 1998.

BACKGROUND OF THE INVENTION

1. Field of the Invention

The present invention relates generally to the fields of lipid/liposome technology and DNA delivery. More specifically, the present invention relates to a stabilization of lipid:DNA formulations during nebulization.

2. Description of the Related Art

The development of liposomal formulations compatible with aerosol delivery has allowed the jet nebulizer to deliver nucleic acids preparations whose biological activity is maintained sufficient for therapeutic use. Utilization of liposomes for aerosol delivery has many advantages, including aqueous compatibility; sustained pulmonary release allowing maintanence therapeutic drug levels; and, further, liposomes facilitate intra-cellular delivery, particularly to respiratory epithelial cells.

The efficacy of localized, topical therapy via aerosols is determined by the amount of drug delivered at the sites of disease within the lung; and there are several different key parameters that determine the amount of delivery which interact to provide the therapeutic efficacy of aerosol formulations. For example, nebulizer design, flow rate, flow volume, particle size, hygroscopicity and the presence of ancillary equipment (tubing, connectors, mouth pieces, face masks, and the like), are important variables. Thus, aerosol output efficiency of appropriate particle sizes can be increased through proper implementation of the proper nebulizer device. Inappropriate implementation of the device and/or imperfect parameters can affect inhaled dosages, delivery sites and influence the therapeutic outcome.

Drug formulation also is a critical factor regulating aerosol output efficiency and aerodynamic properties of drug-liposomes. It has been discovered that drug-liposome output efficiency can be increased through the utilization of liposomes formulated with low phase transition temperatures (see Waldrep et al., *J. of Aerosol Med.* 7:1994 (1994) and Waldrep et al., *Int'l J. of Pharmaceutics* 97:205–12 (1993)). An additional method to increase aerosol drug-liposome output is to increase the drug and phospholipid reservoir concentrations. Nebulization of some drug-liposome formulations at greater than 50 mg/ml results in clogging of the nebulizer jets; yet empty liposomal formulations up to 150 mg/ml have been successfully nebulized (see Thomas, et al., *Chest* 99:1268–70 (1991)). Further, the aerosol performance (output and particle size) i s influenced in part by physiochemical properties such as viscosity and surface tension. Such variables affect the maximal drug-liposome concentrations compatible with aerosol delivery via the jet nebulizer.

A problem associated with the aerosol delivery of cationic lipid:plasmid DNA formulations for the purpose of targeted pulmonary gene therapy is that the process of nebulization leads to a marked decrease in the transfection efficiency of the formulations. This is a major reason for the relatively low in vivo gene transfer efficiency of aerosolized formulations. A rapid loss in activity is associated with a wide variety of jet nebulizers and lipid:DNA formulations.

The prior art is deficient in the lack of effective means of improving the stabilization of lipid:DNA formulations during nebulization. The present invention fulfills this long-standing need and desire in the art.

SUMMARY OF THE INVENTION

The present invention examines liposomes complexed with plasmid DNA by electron microscopy and investigates the effects of liposome-DNA formulation and jet nebulization on liposomal morphology.

In one embodiment of the present invention, there is provided a liposomal aerosol composition, comprising a pharmaceutical compound, a cationic lipid, a neutral co-lipid, and tryptone.

In another embodiment of the present invention, there is provided a liposomal aerosol composition, comprising a pharmaceutical compound, a cationic lipid, a neutral co-lipid, and glutamic acid.

In yet another embodiment of the present invention, there is provided a nebulized cationic lipid:neutral co-lipid:DNA suspension useful for lipid-DNA transfections, wherein the cationic lipid is bis(guanidinium)-tren-cholesterol (BGTC), and the neutral co-lipid is dioleoylphosphatidylethanolamine (DOPE).

In still yet another embodiment of the present invention, aerosol exposure was made more efficient and more effective by holding mice in a closed chamber and exposing to aerosol that was replenished during a one minute period of nebulization out of each 10 minute period. In this design, compressed air containing 5% carbon dioxide was used instead of room air in order to enhance the deep breathing of animals and thereby enhance the lung deposition of the transfection formulations.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A illustrates the levels of β-galactosidase detected for each condition. FIG. 1B illustrates the levels of protein determined for each condition.

FIG. 5A shows that A549 cells were transfected for 6 hours and were harvested and extracted for β-galactosidase analysis 48 hours after initiating transfection. The particle size distribution was determined for each time point by Nicomp light scattering analysis and presented as density-weighted mean particle diameter. The β-galactosidase of cell extracts was compared to the particle size determined for preparations subjected to both sonication and nebulization.

FIG. 5B shows that uptake of DL-EPC:DOPE:$^3$H-pCMVβ was performed as above except that $^3$H-pCMVβ was used in place of pCMVβ. Formulations prepared with unsonicated lipid were 1.3μ (mean diameter) whereas formulations prepared with sonicated lipid were 0.1μ (mean diameter). After a 24 hour exposure to A549 cells, cells were washed repeatedly to remove free radiolabled complex, extracted and counted. The difference between each of the lipid groups and the DNA-only group was extremely significant (P<0.01, paired t-test, n=3) as was the difference between the two lipid groups (P<0.01, paired t-test, n=3).

FIG. 5C shows the effect of particle size on in vivo expression was determined by intranasal instillation of preparations of DL-EPC:DOPE:pCMVβ using either unsonicated or sonicated lipid. As indicated for the uptake studies above, the preparations prepared with unsonicated lipid were 1.3μ (mean diameter) whereas formulations prepared with sonicated lipid were 0.1μ (mean diameter). Equal amounts of DNA (6 μg per instillation) were used for each group. 48 hours after instillation, lungs were removed and tissues processed for CAT activity. The difference between the sonicated and unsonicated groups is extremely significant (P<0.01, paired t-test, n=6).

DETAILED DESCRIPTION OF THE INVENTION

Figure 1A:
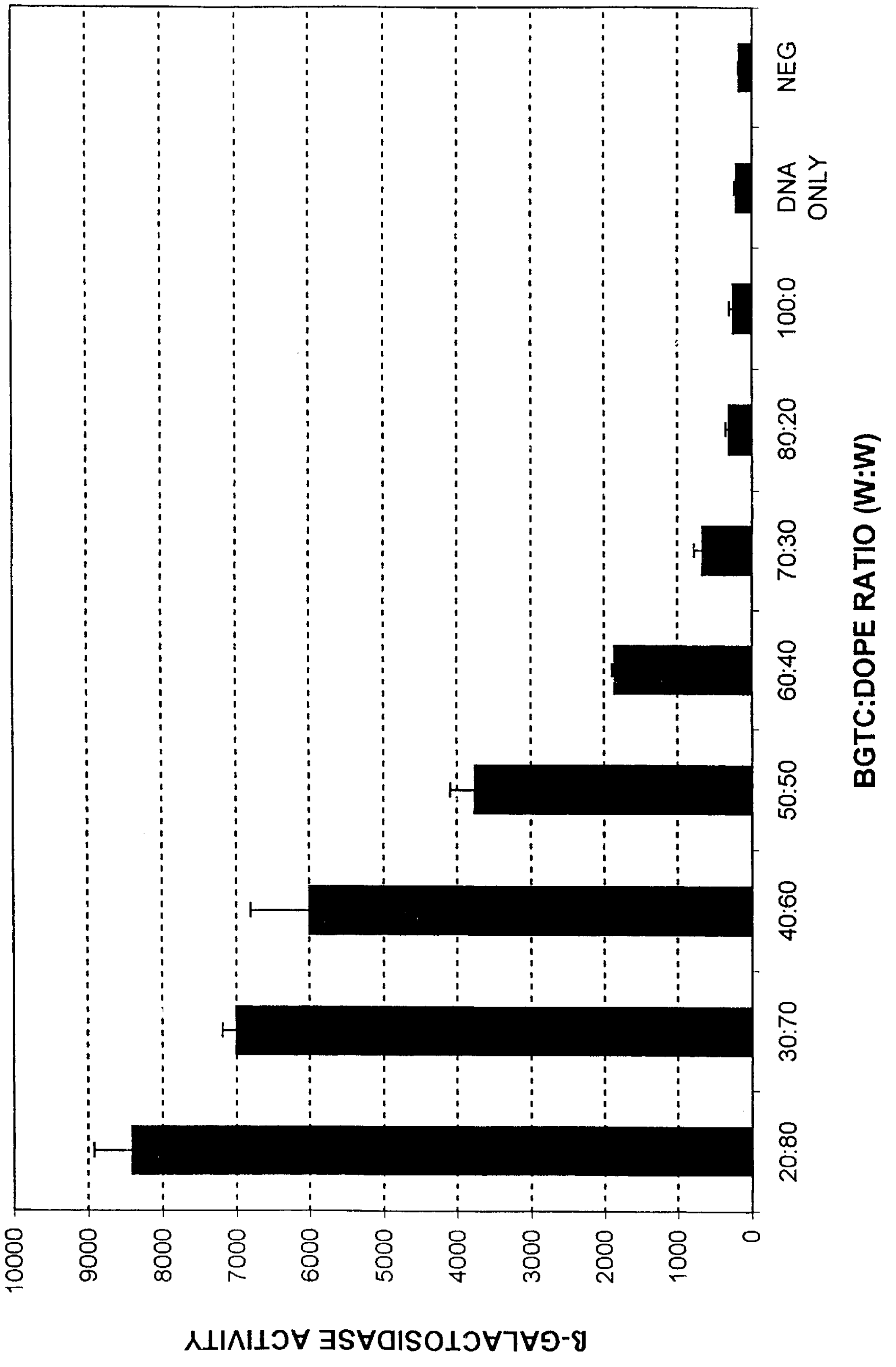
FIGS. 1A and 1B shows transfection of A549 cells with BGTC:DOPE:pCMVβ at various BGTC:DOPE ratios. A constant ratio of lipid to DNA (3:1) and a constant concentration of DNA were used throughout the experiment except for "NEG" which was not transfected, but which were exposed to otherwise identical media changes. A549 cells were transfected for 6 hours and were extracted for β-galactosidase 48 hours after initiating transfection.

The present invention demonstrates the effects of cationic liposome-DNA formulation on both transfection efficiency (in vitro and in vivo) and jet nebulizer stability. The effects of nebulization and sonication on liposome-DNA particle size characteristics were also examined. Electron microscopy of promising formulations was performed using several fixation methods.

The cationic lipid bis-guanidinium-tren-cholesterol (BGTC), in combination with the neutral co-lipid dioleoylphosphatidylethanolamine (DOPE), was found to have a degree of stability adequate to permit effective gene delivery by the aerosol route. Optimal ratios of lipids and plasmid DNA were identified. Particle size analysis and ultrastructural studies revealed a remarkably homogeneous population of distinctly liposomal structures correlating with the highest levels of transfection efficiency and nebulizer stability.

Optimizing gene delivery vectors for pulmonary aerosol delivery to respiratory sites must take into account factors other than transfection efficiency in vitro. Effects of liposome-DNA formulation on liposomal morphology (i.e., particle size, multilamellar structure) appear to be relevant to stability during aerosolization. The present studies make it possible to identify formulations that hold promise for successful clinical application of aerosol gene delivery.

The present invention is directed to a liposomal aerosol composition, comprising a pharmaceutical compound, a cationic lipid, a neutral co-lipid, and tryptone. In one embodiment of this liposome aerosol composition, the pharmaceutical compound is a gene in the form of plasmid DNA. Representative examples of useful lipids include egg yolk phosphatidylcholine, hydrogenated soybean phosphatidylcholine, dimyristoylphosphatidylcholine, dilauroyl-phosphatidylcholine, dioleoylphosphatidylcholine, bis(guanidinium)-tren-cholesterol and dipalmitoyl phosphatidylcholine. The co-lipid is generally a neutral phospholipid. Representative examples of suitable co-lipids include dioleoylphosphatidylethanolamine (DOPE), analogs of dioleoylphosphatidylethanolamine and cholesterol. Typically, the tryptone is found in this composition in an amount sufficient to enhance transfection of a DNA:lipid suspension following nebulization. Generally, such concentrations are from about 0.1% to about 5%.

The present invention is also directed to a liposomal aerosol composition, comprising a pharmaceutical compound, a cationic lipid, a neutral co-lipid, and glutamic acid. In one embodiment of this liposome aerosol composition, the pharmaceutical compound is a gene. Representative examples of useful lipids include egg yolk phosphatidylcholine, hydrogenated soybean phosphatidylcholine, dimyristoylphosphatidylcholine, dilauroyl-phosphatidylcholine, dioleoylphosphatidylcholine, phosphatidylcholine, bis (guanidinium)-tren-cholesterol and dipalmitoyl phosphatidylcholine. Typically, the glutamic acid is found in this composition in an amount sufficient to enhance transfection of a DNA:lipid suspension following nebulization. Generally, such concentrations are from about 0.1% to about 5%.

The present invention is also directed to a nebulized cationic lipid:DNA suspension useful for lipid-DNA transfections, wherein said cationic lipid is bis (guanidinium)-tren-cholesterol and the neutral co-lipid is DOPE. Preferably, the bis(guanidinium)-tren-cholesterol/DOPE is contained in said suspension in a concentration relative to the plasmid DNA concentration determined to be optimal for transfection. The concentraton of the stable formulation depends on the relative concentrations of the three components, i.e., the plasmid DNA, the cationic lipid bis(guanidinium)-tren-cholesterol, and the neutral co-lipid DOPE. A preferred range of the plasmid DNA is from about 1 μg/ml to about 1000 μg/ml.

The optimal ratio of plasmid DNA to combined lipid (lipid formulation includes a 1:1 ratio of cationic lipid to neutral co-lipid) is approximately from 1:3 to 1:5. However, slightly different ratios often prove optimal for different applications or different plasmids, e.g., larger plasmids have a greater net charge and therefore require more lipid to neutralize this charge. Therefore, for 400 μg/ml DNA, one would use approximately 600 μg/ml of bis(guanidinium)-tren-cholesterol and 600 μg/ml of DOPE. Concentrations of bis(guanidinium)-tren-cholesterol up to about 1.5 mg/ml (when present in a 1:1 ratio of DOPE) should be stable in a formulation with plasmid DNA. In one embodiment of the nebulized cationic lipid:DNA suspension of the present invention, the ratio of DNA concentration to combined cationic lipid and neutral co-lipid concentration is from about 1:1 to about 1:4.

The following examples are given for the purpose of illustrating various embodiments of the invention and are not meant to limit the present invention in any fashion.

EXAMPLE 1

Plasmid DNA

The cytomegalovirus promoter (CMV) with the *E. coli* β-galactosidase reporter gene (pCMVβ; CLONTECH, Palo Alto, Calif.) was used to assess mammalian cell expression in vitro. An efficient chloramphenicol acetyltransferase gene (pCMVHiCAT; a gift of Genzyme, Inc., Framingham, Mass.) was used to assess transfection efficiency in vivo. Bacterial cultures were transformed with the above plasmids and bulk quantities of plasmid DNA were produced and purified on Qiagen columns (Qiagen, Inc., Chatsworth, Calif.). [$^3$H]-labeled DNA was prepared in an identical fashion except that bacterial cultures were grown in the presence of [$^3$H]thymidine.

EXAMPLE 2

Synthesis of Cationic Lipids

The cationic lipids were synthesized. DC-cholesterol (3β-[N-[(N',N'-dimethyl-amino)ethane]carbamoyl]cholesterol) was synthesized according to the methods of Gao and Huang (5). GL-67 ($N^4$-spermine cholesteryl carbamate) was synthesized according to the method of Lee et al. (7). Guanidinium cholesterol bis-guanidinium-tren-cholesterol (BGTC) was synthesized according to the methods of Vigneron et al. (11). N-(2-hydroxyethyl)-N,N-dimethyl-2,3-bis (tetradecytoxy)-1-propanaminium bromide (DMRIE) was obtained from Vical (San Diego, Calif.). Dioleoyl trimethylammonium propane (DOTAP) and 1,2-dilauroyl-sn-glycero-3-ethylphosphocholine (DL-EPC) were gifts of Avanti Polar Lipids (Alabaster, Ala.). Other reagents were from Sigma (St. Louis, Mo.).

EXAMPLE 3

Preparation of Cationic Lipid:Neutral Co-lipid:DNA Complexes

All of the cationic lipid:DOPE formulations were prepared by first mixing the cationic lipid (5 mg/ml in chloroform) with an appropriate volume of dioleoyl phosphatidyl-ethanolamine (DOPE; Avanti Polar Lipids; 5 mg/ml in chloroform) and drying under nitrogen. The lipid mixture was dissolved in t-butanol at 37° C., frozen at −80° C., and lyophilized for at least 24 hours. The lipids were stored at −20° C. until use, at which time they were warmed to room temperature and resuspended in sterile water (Water for Irrigation (WFI; Baxter, Deerfield, Ill.)) for at least 30 minutes prior to complexing with DNA. Lyophilized BGTC-:DOPE formulations appeared to be stable at −20° C. over a period of 6–8 months or more. The lipid:DNA formulations were prepared by diluting the DNA in water and slowly adding to the lipid dispersion while gently vortexing. The material was allowed to incubate at room temperature for 15–30 minutes before use.

Except where indicated, lipids were not sonicated prior to complexing with DNA since the process of jet nebulization acts as an "extrusion" process and results in a size range of lipid:DNA particles optimal for transfection. If aggregation was observed with any of the preparations, it was not used. The lipid:DNA preparations were then inspected visually and/or by Nicomp particle size analysis (see below) to determine approximate particle size characteristics prior to use. Since changes in the relative proportion of neutral co-lipids can have an effect on transfection efficiency, nebulizer stability and liposomal morphology without necessarily changing the charge ratio, ratios throughout will be by weight. However, since the resulting charge ratio of complexes is also important in understanding the role that formulation plays in aerosol transfection stability, this ratio (BGTC guanidinium/DNA phosphate ratio) will, where appropriate, be included in parentheses. This was determined according to Vigneron et al. (11), by assuming that 1 μg of DNA is 3 nmol of negatively charged phosphate and that only two guanidinium groups (and not the tertiary amine) of BGTC are positively charged at neutral pH.

EXAMPLE 4

Optimizing DNA to Lipid Ratios

Optimization of DNA to lipid ratio was determined by in vitro transfection. An estimate of the range of optimal DNA:lipid ratios for experimental examination in cell culture was determined by charge ratio and further verified by gel electrophoresis. A ratio of DNA:lipid from 1:1 to 1:10 (w:w) was run on a 1% Agarose-TAE gel. When the negative DNA charge is completely neutralized by the cationic lipid (resulting in no migration of the DNA in the gel), tissue culture transfection is generally close to optimal and provides a range of DNA:lipid ratios to evaluate experimentally. Generally, a DNA:lipid (BGTC:DOPE at 50:50) ratio of 1:3 to 1:4 by weight (1.4:1 to 1.9:1 by BGTC guanidinium:DNA phosphate ratio) resulted in no migration into the gel.

EXAMPLE 5

Tissue Culture

A549 is a human lung carcinoma cell line with epithelial-like morphology that has been used extensively for the screening of cationic lipid-based formulations (1). Cell lines were purchased from the American Type Culture Collection (Rockville, Md.). These cells were cultured in Dulbecco's Modified Essential Medium (D-MEM) supplemented with 10% defined fetal bovine serum (FBS), 2 mM L-glutamine, and 50 μg/ml gentamicin (unless otherwise noted). Cells were cultured in a cell culture incubator at 37° C. and in the presence of 5% $CO_2$. Only the first 8 passages of cells were used.

EXAMPLE 6

In vitro Transfection

Cells were plated at $1.5\times10^5$ cells/35-mm dish the day prior to transfection (unless otherwise noted). Cells were approximately 80% confluent at the time of transfection. After lipid:DNA complexing was complete (see above), the liposomal-DNA formulations were brought up in Opti-mem I Reduced Serum Medium (Opti-mem; Gibco-BRL, Grand Island, N.Y.) to a final DNA concentration of 1 μg/ml. Immediately prior to transfection, cells were rinsed with Opti-mem and then overlaid with the 1 ml of the transfection solution per well (at least 3 wells were transfected for each time point or condition). After 24 hours (except where a shorter transfection time is indicated) the transfection solution was removed, the cells were rinsed, and 1 ml of supplemented D-MEM medium (see above) was added. The cells were then incubated for an additional 24 hours, rinsed two times with phosphate buffered saline (PBS) and then lysed using a lysis buffer (.1 M Tris-HCl, 0.5% Triton X-100, Sigma, St. Louis, Mo.).

EXAMPLE 7

Quantitative Analysis of β-galactosidase Transfection Efficiency

Following lysis of cells, the protein concentration of the lysate was determined using the BCA Protein Assay from Pierce (Rockford, Ill.). The β-galactosidase activity was quantified by using a chlorophenolred-β-D-galactopyranoside (CPRG; Boehringer Mannheim, Indianapolis, Ind.) assay in a 96 well plate format and read on a Dynatech MR5000 microtiter plate reader (Dynatech Laboratories, Inc., Chantilly, Va.).

EXAMPLE 8

In vitro Effects of Lipid Sonication on Liposome-DNA Particle Size and Transfection Efficiency Lipid formulations prepared as described above (excluding DNA) were sonicated for the times indicated in a Branson 2210 Bath Sonicator at room temperature at approximately one half maximum power. Aliquots were removed at varying intervals of time, complexed with plasmid DNA (either pCMVβ or pCMVHiCAT) and then used to transfect A549 cells as described above. Particle size analysis was performed on lipid before and after complexing with DNA.

EXAMPLE 9

In vitro Stability of Nebulized Liposome-DNA Complexes

The lipid:DNA formulations were prepared by diluting the DNA to 80 μg/ml in 2.5 ml WFI, adding the appropriate amount of lipid in 2.5 ml WFI and incubating at room temperature for 15–30 minutes before nebulizing. At the time intervals indicated, 50–75 μl aliquots from the nebulizer reservoir were removed and prepared for transfection as described above. It should be noted that for jet nebulizers to produce small particle aerosols they must recycle nebulizer liquid continuously, since only a minute fraction of the nebulizer fluid (usually less than 0.1%) is released as aerosol with each pass through the nebulizer jet. Most of the droplets (about 99.92%) are impacted on the wall of the enclosing flask and reflux to the reservoir (14). Large lipid:DNA particles (>400 nm) are rapidly processed into smaller particles so that within a short time, the lipid:DNA particle size within the nebulizer reservoir becomes very similar to that of aerosol particles (such as those collected by an all glass impinger (AGI-4, Ace Glass Co., Vineland, N.J.)). The Puritan Bennett 1600 nebulizer (Carlsbad, Calif.) was modified by removing one tube from the twin jets (which resulted in enhanced output for lung deposition at a slower rate for animal studies) and is referred to as the Puritan Bennett 1600 single jet (PB sj). The Puritan Bennett 1600 single jet was run at a flow rate of 8 L/min unless otherwise indicated.

EXAMPLE 10

In vivo Transfection with Liposome-DNA Aerosol

Lipid:DNA formulations were prepared as described above except that the concentration of DNA was increased to 2 mg per 20 ml (after addition of the appropriate concentration of liposomes) for one nebulizer dose. The droplets containing liposome-DNA complexes had a mass median aerodynamic diameter (MMAD) of about 1.5 microns as determined by Andersen Cascade Impactor analysis. The outflow of the nebulizer was passed through a sealed plastic cage (13×17×30 cm.) which housed the mice (usually 6–8 animals per group). Air exited this chamber through a HEPA filter and the entire apparatus was situated under a laminar flow hood vented through additional HEPA filtration to the outside.

Unlike the in vitro experiments, nebulization used 5% $CO_2$/95% air, instead of compressed room air, in order to stimulate deeper breathing by the mice being exposed to the aerosol. This had no effect on the liposome-DNA complexes. To minimize the use of aerosol, the nebulizer was operated for only one minute in each 10 minutes. Once the first 20 mls of suspension was consumed, the nebulizer was replenished with an additional 20 mls at the same concentration. The exposure required approximately 12 hours, during which time the mice were supplied with food and water and allowed to move freely about the chamber.

Generation of aerosols of liposome preparations with various drugs, DNA and various lipids, and their deposition in the respiratory tract of man and animals follow general principles. Many details of the formulation, nebulization and deposition of inhaled droplets of aerosols containing a number of different preparations of liposome-drug preparations and of liposomes alone are described elsewhere (15–18).

EXAMPLE 11

Quantitative Analysis of CAT Expression in vivo:

CAT expression was found to be a more sensitive means of measuring transfection efficiency in vivo. Animals that were exposed to nebulized formulations as described above were sacrificed at appropriate time points (usually 48 hours unless otherwise indicated) and the lungs and trachea were removed and frozen in liquid nitrogen. The tissues were later minced in lysis buffer and homogenized using a Wig-L-Bug bead homogenizer (Crescent Dental Mfg., Lyons, Ill.). The tissue extracts were analyzed for CAT content using a commercially available CAT ELISA kit (Boehringer Mannheim Gmbh, Germany). The results obtained with the ELISA assay were equivalent or better than those obtained using conventional TLC methods and organic phase separation methods. Because of the variability observed with virtually all in vivo aerosol studies, experimental and control groups usually consisted of 6–8 animals.

EXAMPLE 12

Particle Size Analysis of Liposome-DNA Complexes

Liposome-DNA particle size was determined by analyzing the formulations dispersed in aqueous media with dynamic light scattering using a Nicomp Model 370 Submicron Particle Sizer (Particle Sizing Systems, Inc., Santa Barbara, Calif.) and by electron microscopy (see below).

EXAMPLE 13

Ultrastructural Analysis of Liposome-DNA Complexes by Electron Microscopy

Negative Stain: Liposome or liposome-DNA suspensions were allowed to settle for 1 min on carbon and formvar coated copper grids. After blotting excess fluid, a series of drops of 2% uranyl acetate was applied and blotted off. A thin film of the uranyl acetate solution was allowed to dry on the grid.

Chemical Fixation and Sectioning: Liposome or liposome-DNA suspensions were mixed with an equal volume of 2% osmium tetroxide and fixed for 30 min at 4° C., then centrifuged into a pellet. The fixed pellets were dehydrated in a graded acetone series, then infiltrated with Epon-Araldite resin and polymerized. Blocks were sectioned at a thickness of 60 nm. The sections were stained with uranyl acetate and lead citrate.

Cryofixation and Sectioning: Dextran (39 kD, Sigma) was added to liposome or liposome-DNA suspensions to a final concentration of 15% (w/v) as a cryoprotectant. Aliquots of the samples were rapidly frozen in a Balzers HPM-010 high pressure freezing apparatus, then freeze-substituted in 2% osmium tetroxide in acetone at −80° C. for 2 days. To complete fixation, the samples in freeze-substitution medium were warmed to −20° C. for 4 hr, then to 4° C. for 2 hr and room temperature for 1 hr. The fixed, dehydrated samples were then embedded, sectioned and stained as above. All preparations were imaged on a Philips CM 10 or JEOL 100 CX transmission electron microscope operating at 80 kV.

Statistics: Comparison of data sets utilized the paired t-test, two tailed (InStat Biostatistics, 1990–92, GraphPad Software, Inc.).

EXAMPLE 14

In vitro Characterization of the Transfecting Activity of Different Ratios of the Constituents of Guanidinium-cholesterol:DOPE:DNA Complexes Although in vitro transfection systems are not always indicators of successful transfection in vivo, in vitro transfection screenings can rapidly and reproducibly provide useful preliminary data regarding lipid:DNA formulation modifications or the stability of formulations during jet nebulization. FIG. 1A shows the transfecting activity of lipid:pCMVβ complexes through a range of BGTC concentrations tested in A549 cells when the lipid:DNA ratio is kept constant. The concentration of the co-lipid, DOPE, was reciprocal to BGTC concentrations and, therefore, the charge ratio will also vary in these formulations. β-galactosidase activity of the cell extract measured by CPRG assay was negligible when the BGTC concentration was less than 20% and the DOPE concentration was greater than 80%, but reached a high value when the BGTC concentration reached 20%. The low values are likely due to aggregation associated with high concentrations of DOPE and a decreasing BGTC guanidinium:DNA phosphate ratio. In vitro transfecting activity was optimal when the BGTC concentration was 20% and the DOPE concentration was 80%, then declined with further increase in BGTC concentration and a corresponding decrease in DOPE. At ratios of BGTC above 70% there was no significant transfecting activity.

Figure 1B:
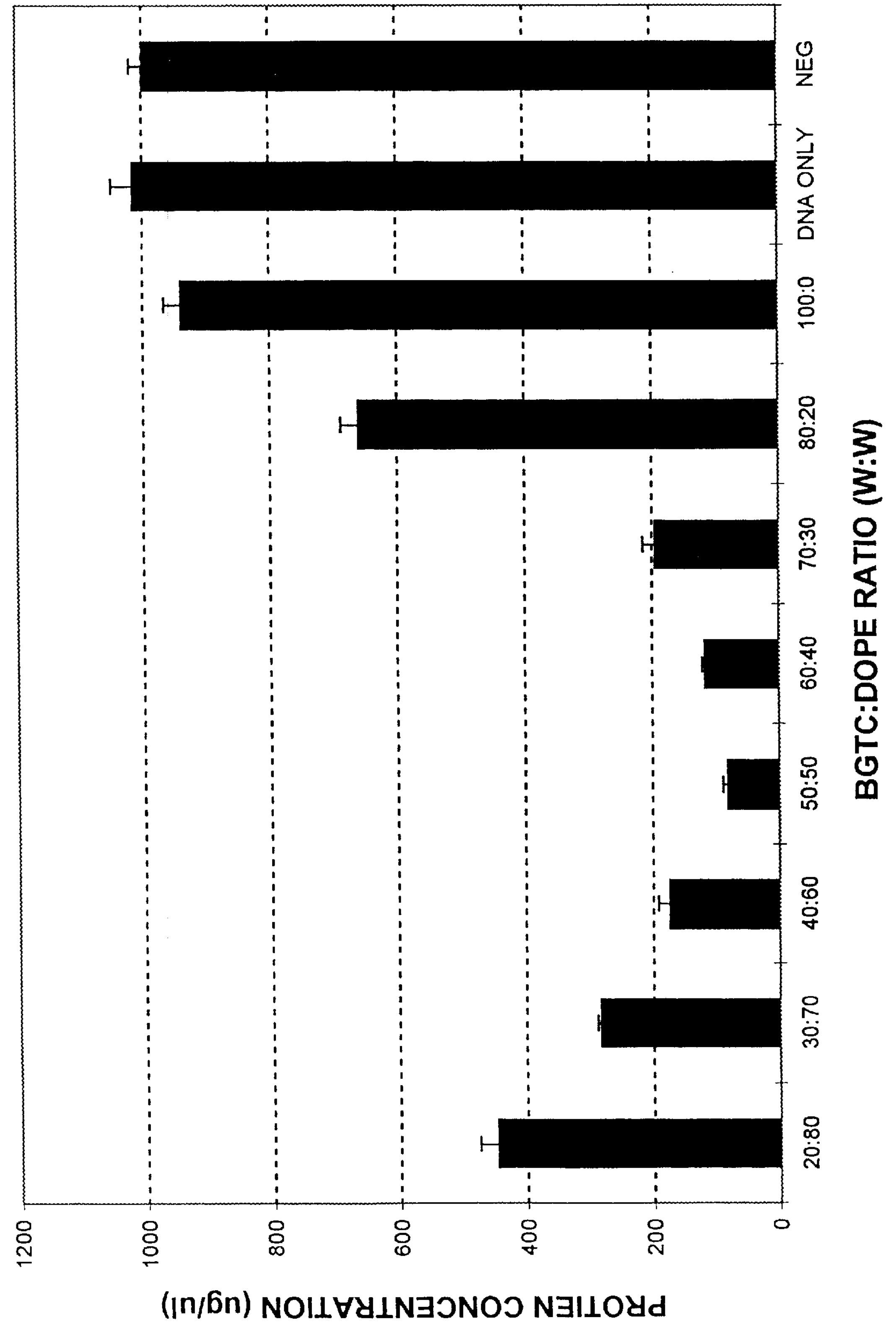

Transfection by BGTC:DOPE formulations was associated with a reduction in cell number manifested by a reduction in protein recoverable from the cell extract (FIG. 1B). Values for total protein were approximately reciprocal to β-galactosidase activity. While this reduction in protein associated with transfection may be in part due to toxicity of the liposome-DNA formulation, studies indicate that the expression of β-galactosidase may inhibit A549 cell proliferation.

EXAMPLE 15

Effect of DNA-lipid Ratios on BGTC:DOPE:pCMVβ Transfection Efficiency

Figure 2:
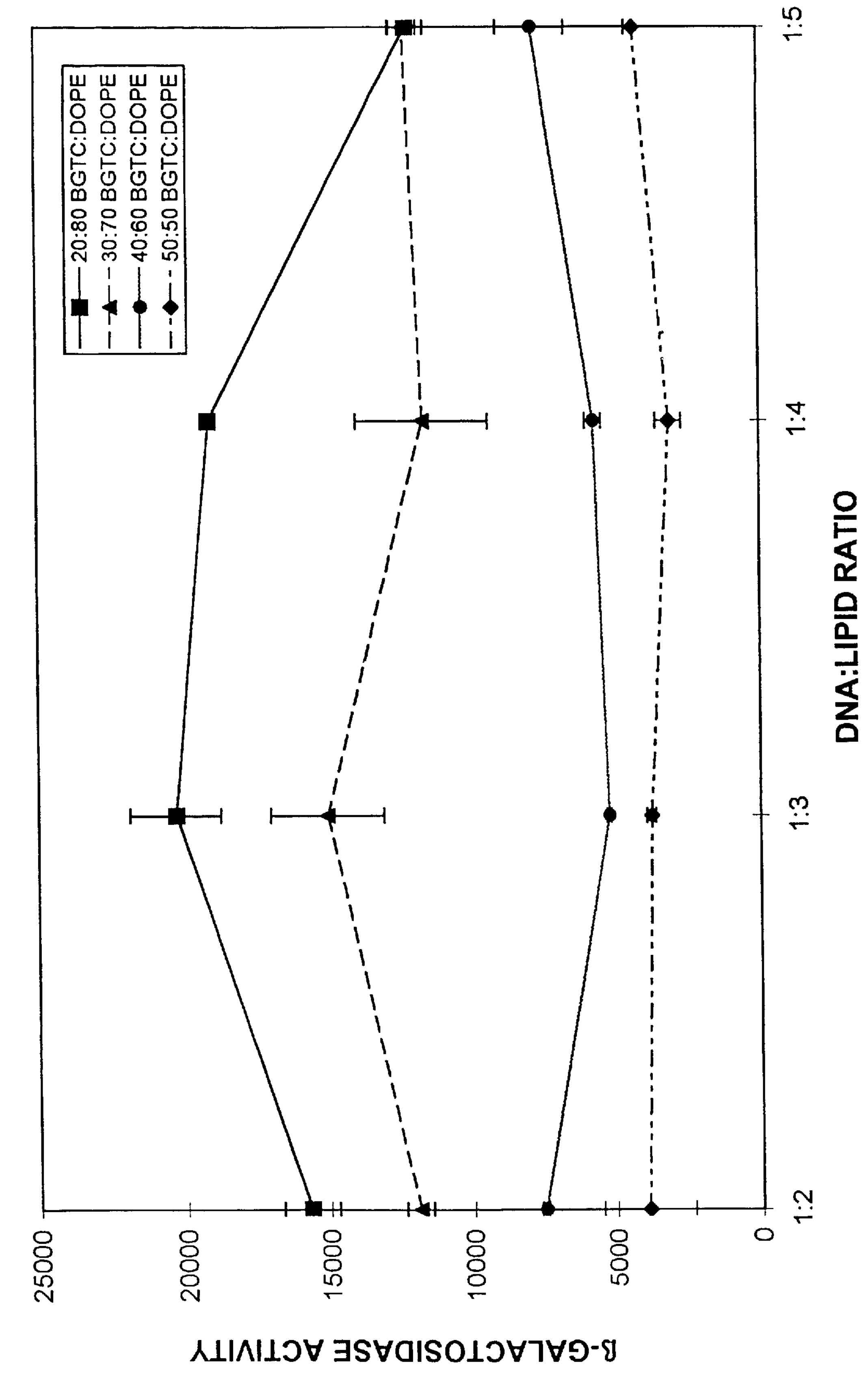
FIG. 2 shows transfection of A549 cells with BGTC:DOPE:pCMVβ at various BGTC:DOPE ratios and at 1:2 to 1:5 DNA:lipid ratios. BGTC percentages varied from 20% to 50% of total lipid. A constant concentration of DNA was used throughout the experiment (1 μg/well of cells in a 12 well plate). A549 cells were transfected for 6 hours and were extracted and analyzed for β-galactosidase activity 48 hours after initiating transfection. Values for different DNA:lipid ratios are not significantly different for each BGTC:DOPE ratio (P>0.05, paired t-test, n=3) except the 20:80 BGTC:DOPE where 1:3 and 1:4 are significantly greater than 1:2 and 1:5 (P<0.01, paired t-test, n=3).

FIG. 2 shows β-galactosidase activity when the DNA:lipid ratios vary from 1:2 to 1:5 by weight (charge ratios are indicated in the figure legend). Since the best results were obtained above with BGTC:DOPE ratios of 20:80 to 50:50, FIG. 2 also shows the effect of different ratios of DNA to lipid on transfection efficiency. The highest transfecting activity is associated with the 20:80 BGTC-:DOPE ratio through the range of DNA:lipid ratios 1:3 to 1:4. This represents a range of charge ratio from only 0.56:1 to 0.75:1 BGTC guanidinium:DNA phosphate. At the 1:5 DNA:lipid ratio the 20:80 and 30:70 BGTC:DOPE ratios show equal transfecting activity, and still greater activity than ratios which contain a larger percentage of BGTC. It is notable that there was relatively little change in in vitro transfection efficiency across the greater than 2-fold range of DNA:lipid ratios examined here.

EXAMPLE 16

Effect of Nebulization on In vitro Transfection Efficiency of BGTC:DOPE:pCMVβ

Figure 3:
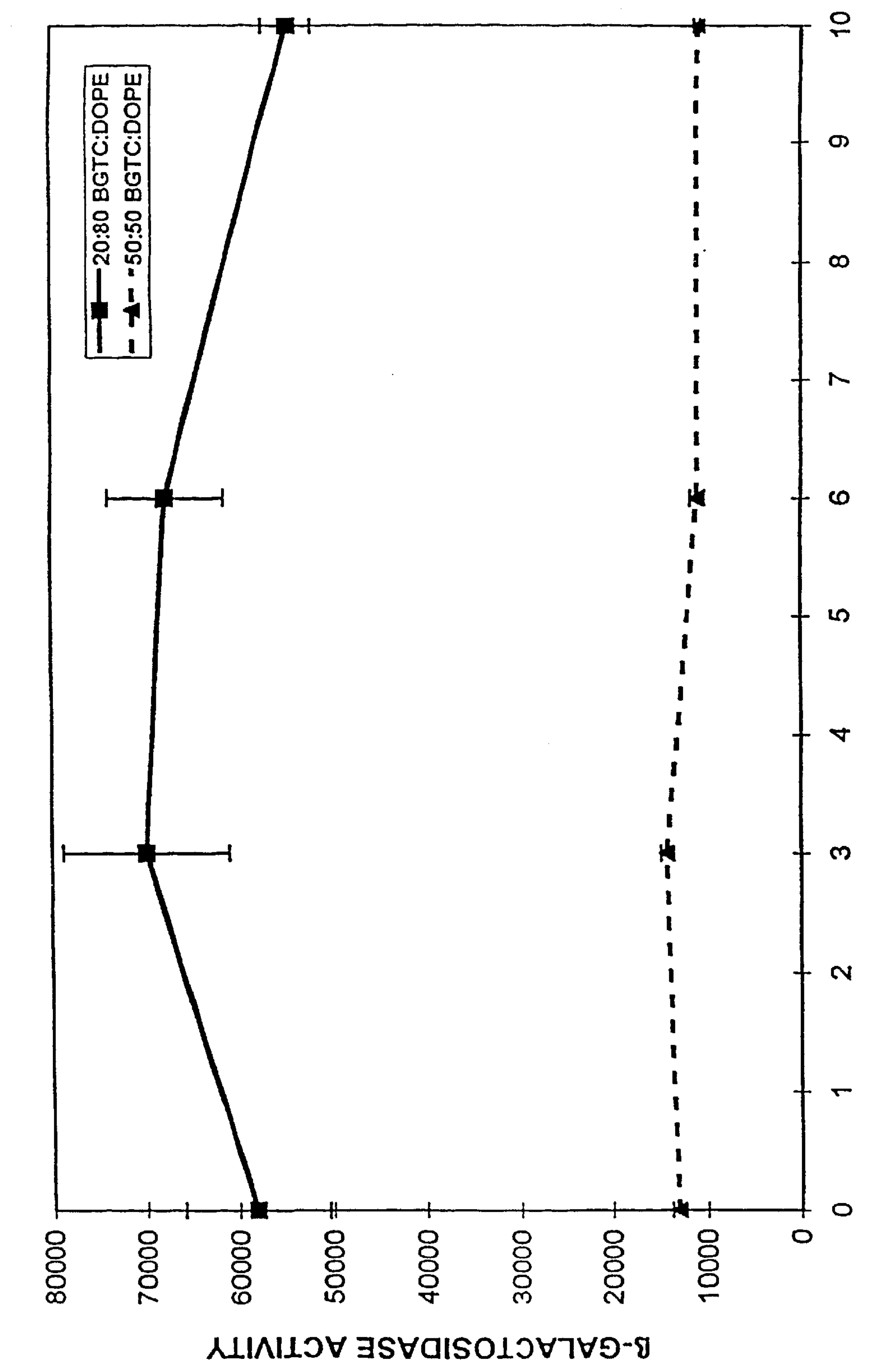
FIG. 3 shows the effect of nebulization on in vitro transfection efficiency of BGTC:DOPE:pCMVβ in A549 cells at two BGTC:DOPE ratios. BGTC:DOPE formulations (50:50 and 20:80 by weight) were prepared using a constant concentration of pCMVβ DNA and a constant DNA:lipid ratio of 1:3. 5 ml of each resulting suspension was nebulized in a Puritan Bennet sj nebulizer at 15 L/min. Aliquots were taken from the nebulizer reservoir at time points indicated. A549 cells were transfected for 24 hours and were extracted for β-galactosidase analysis 48 hours after initiating transfection. Values for each formulation are not significantly different from 0 min (nonnebulized) control (P>0.05, paired t-test, n=3).

Preparations of BGTC:DOPE:pCMVβ liposome complexes in 0.6:2.4:1 and 1.5:1.5:1 ratios by weight (0.56:1 and 1.4:1 by BGTC guanidinium:DNA phosphate) were tested for transfection efficiency over a 10 minute period of nebulization (FIG. 3). The 0.6:2.4:1 preparation (equivalent to the 20:80 BGTC:DOPE in studies above) showed uniformly greater transfecting capacity but both preparations maintained nearly maximum activity over the 10-minute period of nebulization.

Figure 4:
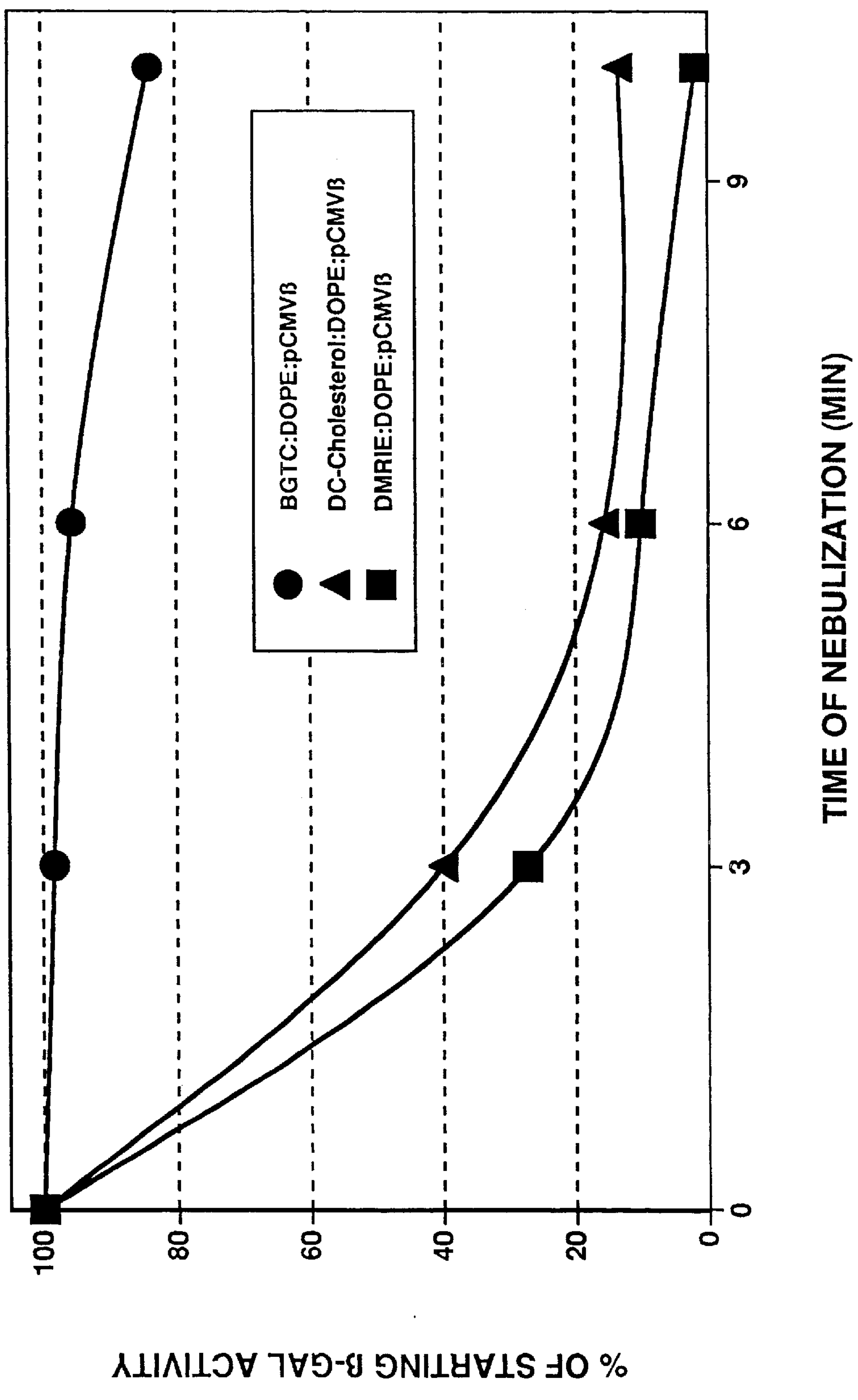
FIG. 4 shows the effect of nebulization on in vitro transfection efficiency of BGTC:DOPE:pCMVβ, DC-cholesterol:DOPE:pCMVβ and DMRIE:DOPE:pCMVβ in A549 cells. BGTC:DOPE:pCMVβ (1.5:1.5:1), DC-cholesterol:DOPE:pCMVβ (2:2:1) and DMRIE:DOPE:pCMVβ (3:3:1) were prepared using a constant concentration of pCMVβ DNA and a constant DNA:lipid ratio. Five ml of each resulting suspension were subjected to nebulization in a Puritan Bennet sj nebulizer at 8 L/min. Aliquots were taken from the nebulizer reservoir at time points indicated. A549 cells were transfected for 24 hours and were extracted for β-galactosidase analysis 48 hours after initiating transfection.

For comparison, the preparation of BGTC:DOPE:pCMVβ (1.5:1.5:1), a preparation of DC-cholesterol:DOPE:pCMVβ (2:2:1) and a preparation of DMRIE:DOPE:pCMVβ (3:3:1) were nebulized for 9–10 minutes (FIG. 4). The formulations of DC-cholesterol:DOPE and DMRIE:DOPE used here were optimized for in vitro transfection of A549 cells and the ratio of DC-cholesterol:DOPE used is similar to that reported elsewhere to be optimal for cell culture transfection (5). There was only a slight loss of the β-galactosidase activity of the BGTC:DOPE:pCMVβ preparation at a nebulizer flow rate of 8 L/min whereas the DC-cholesterol:DOPE:pCMVβ preparation lost 60% of its activity in 3 minutes and was virtually inactive thereafter. The activity of DMRIE:DOPE:pCMVβ was reduced by over 70% after 3 minutes and about 90% after 6 minutes. At higher nebulizer flow rates, the loss of transfection efficiency with formulations involving other cationic lipids (1) is even greater. However, as indicated by the data shown in FIG. 6, BGTC:DOPE-based formulations appear to be stable even at higher nebulizer flow rates.

EXAMPLE 17

Effect of Sonication of Aqueous Dispersions of BGTC:DOPE on BGTC:DOPE:pCMVβ Transfection Efficiency Sonication of cationic lipid: co-lipid formulations generally results in a decrease in the size of subsequently formed liposome-DNA complexes and is often performed to ensure a more homogeneous and consistent preparation for gene therapy applications. Since a similar decrease in liposome-DNA complex diameter results from the nebulization process, sonication is used here to simulate the change in size of liposomes associated with nebulization while eliminating the possibility of DNA shearing. A decrease was observed in transfection efficiency for a number of cationic lipids associated with a reduction in liposome-DNA particle size, such as that associated with sonication.

Figure 5A:
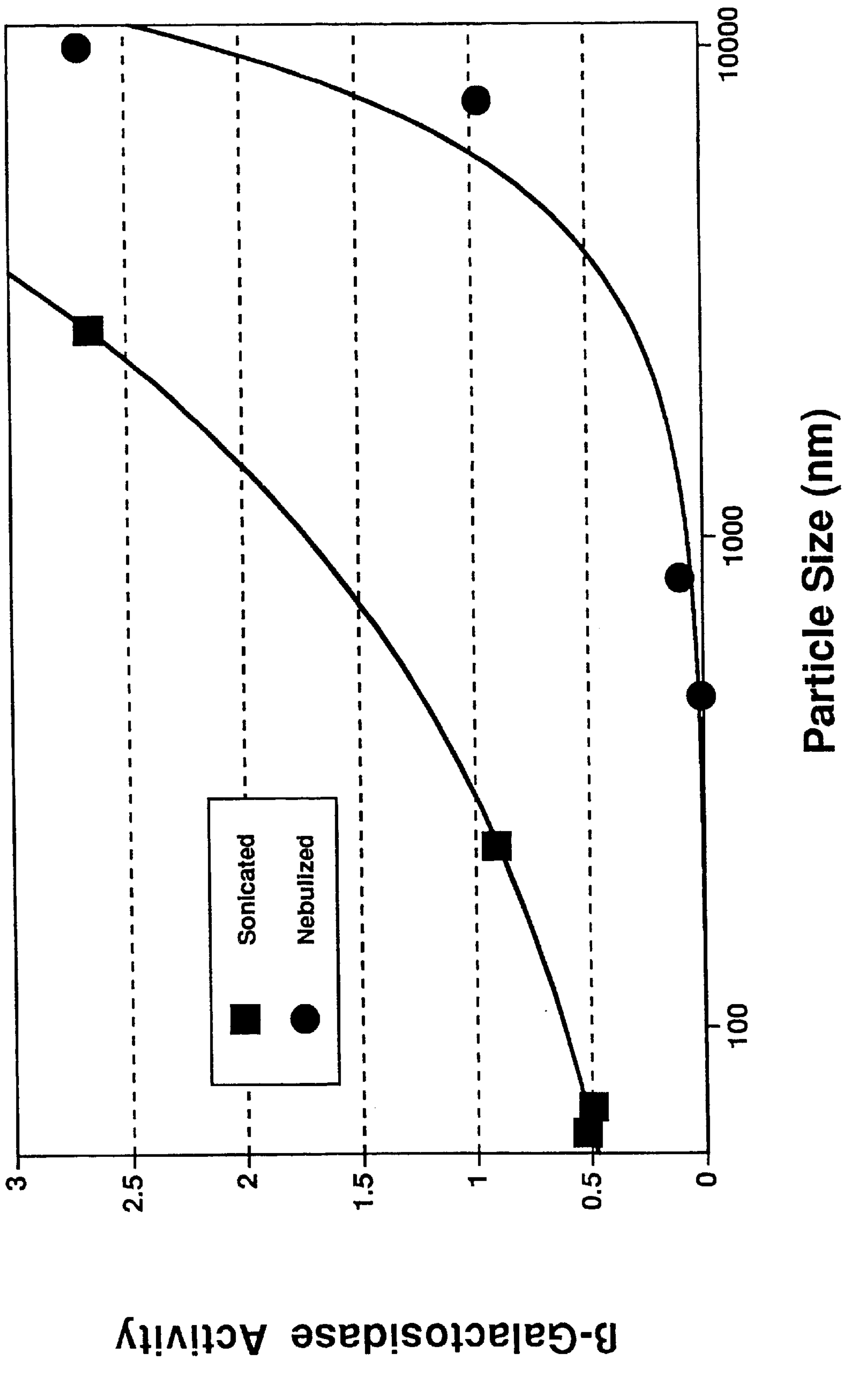
FIGS. 5A–5C shows effect of sonication- and nebulization-induced particle size change on transfection efficiency and DNA uptake in vitro in A549 cells and in vivo transfection efficiency of DL-EPC:DOPE formulations in mouse lung. DL-EPC:DOPE (1:1) was formulated. The lipid was subjected to sonication and aliquots were taken at timed intervals indicated for particle size analysis and determination of transfection efficiency. pCMVβ plasmid DNA was complexed with the lipid samples after sonication. A constant concentration of DNA was used throughout the experiment. Nebulization of preformed DL-EPC:DOPE:pCMVβ complexes was performed as above (Puritan Bennett sj nebulizer at 8 L/min) and aliquots were collected from the nebulizer reservoir at time intervals for particle size analysis and transfection evaluation.

FIG. 5A illustrates the relationship between particle size and transfection efficiency for one such typical cationic lipid-based formulation, DL-EPC:DOPE:pCMVβ, when the preparation is either sonicated prior to complex formation or nebulized after complex formation. It should be noted that sonication of the lipid component occurs prior to complexing with DNA since sonication of liposomes already complexed with DNA destroys all transfecting activity. Although there are clear differences in the levels of transfection obtained with sonicated vs. nebulized complexes, there is clearly a decrease in transfection efficiency associated with decreased particle size.

Figure 5B:
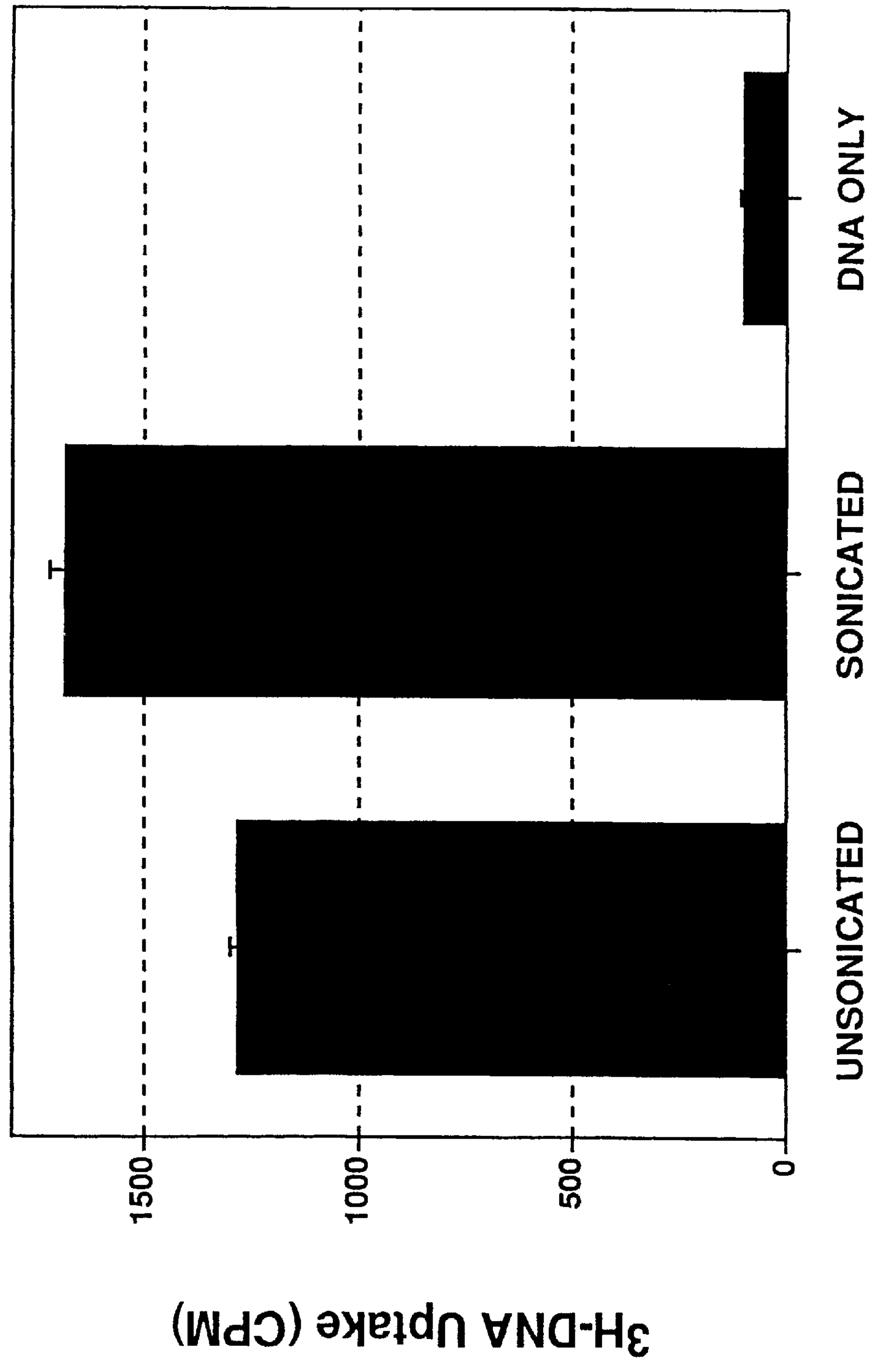

Since there is a possibility that this correlation between DNA liposome size and transfection in vitro could be due, in part, to increased sedimentation of larger particles in an in vitro culture dish, the uptake of radiolabeled plasmid DNA ([$^3$H]pCMVβ) was examined when complexed with sonicated or unsonicated lipids (FIG. 5B, DL-EPC:DOPE:pCMVβ complexes prepared as above). Despite extensive washing of the cells to remove as much of the loosely associated lipid:DNA complex from the surface of cells as possible, there was a higher level of (sonicated lipid):DNA than (unsonicated lipid):DNA associated with the cells, indicating that the particle size-transfection correlation was not likely to be due merely to increased association of larger particles with adherent cells plated in culture dishes.

Figure 5C:
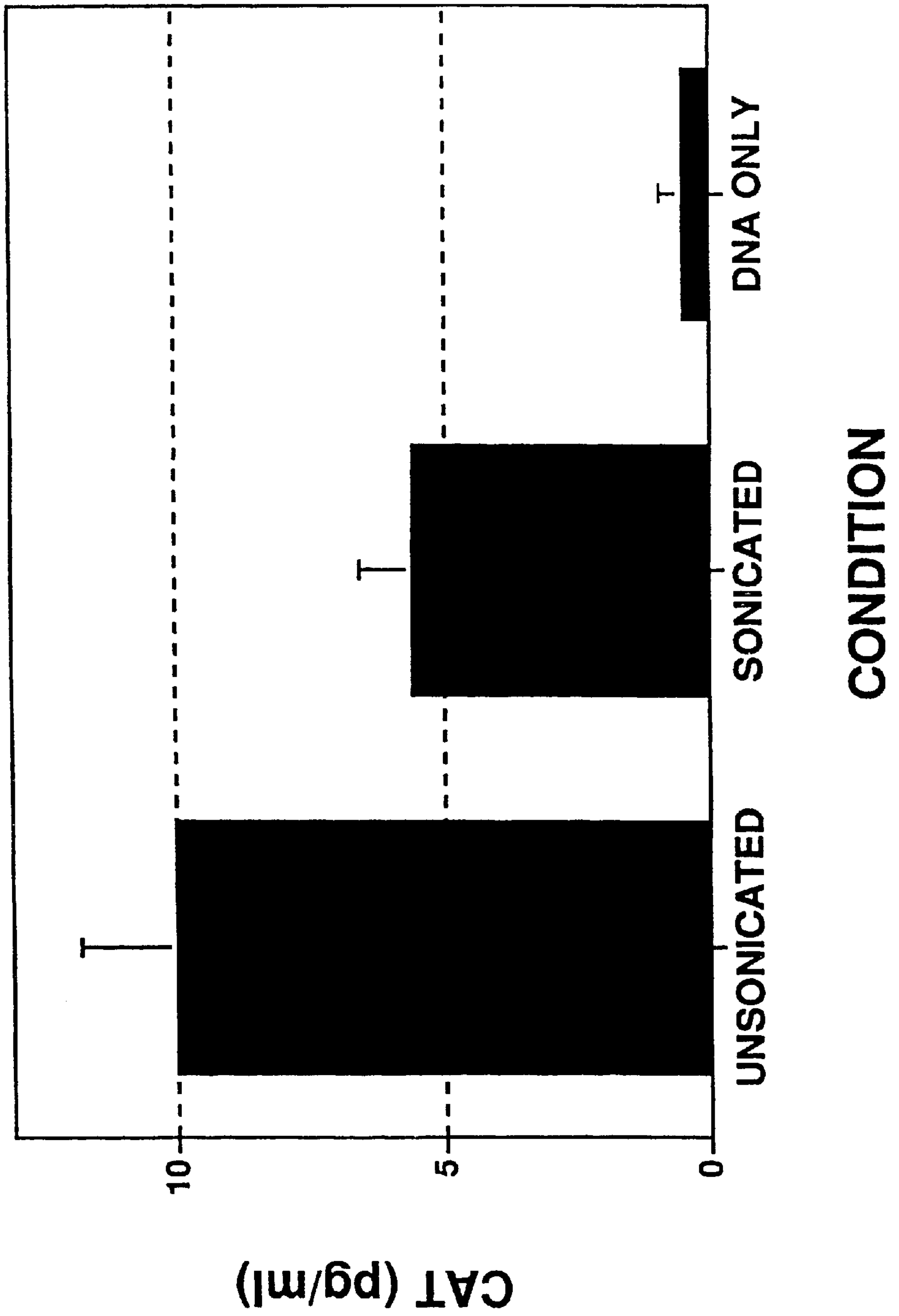

The effect of a sonication-induced decrease in particle size on in vivo transfection (using DL-EPC:DOPE:pCMVHiCAT, 1.5:1.5:1 w:w:w) was also examined in mouse lung by intranasal instillation (FIG. 5C). Instillation was used here to allow the delivery of a defined dose of lipid:DNA to the lungs and airways without the modification of particle size that would occur if the formulations were nebulized. The larger (unsonicated) particles resulted in a roughly 2-fold increase in in vivo transfection efficiency over that obtained with the smaller (sonicated) complexes.

Figure 6:
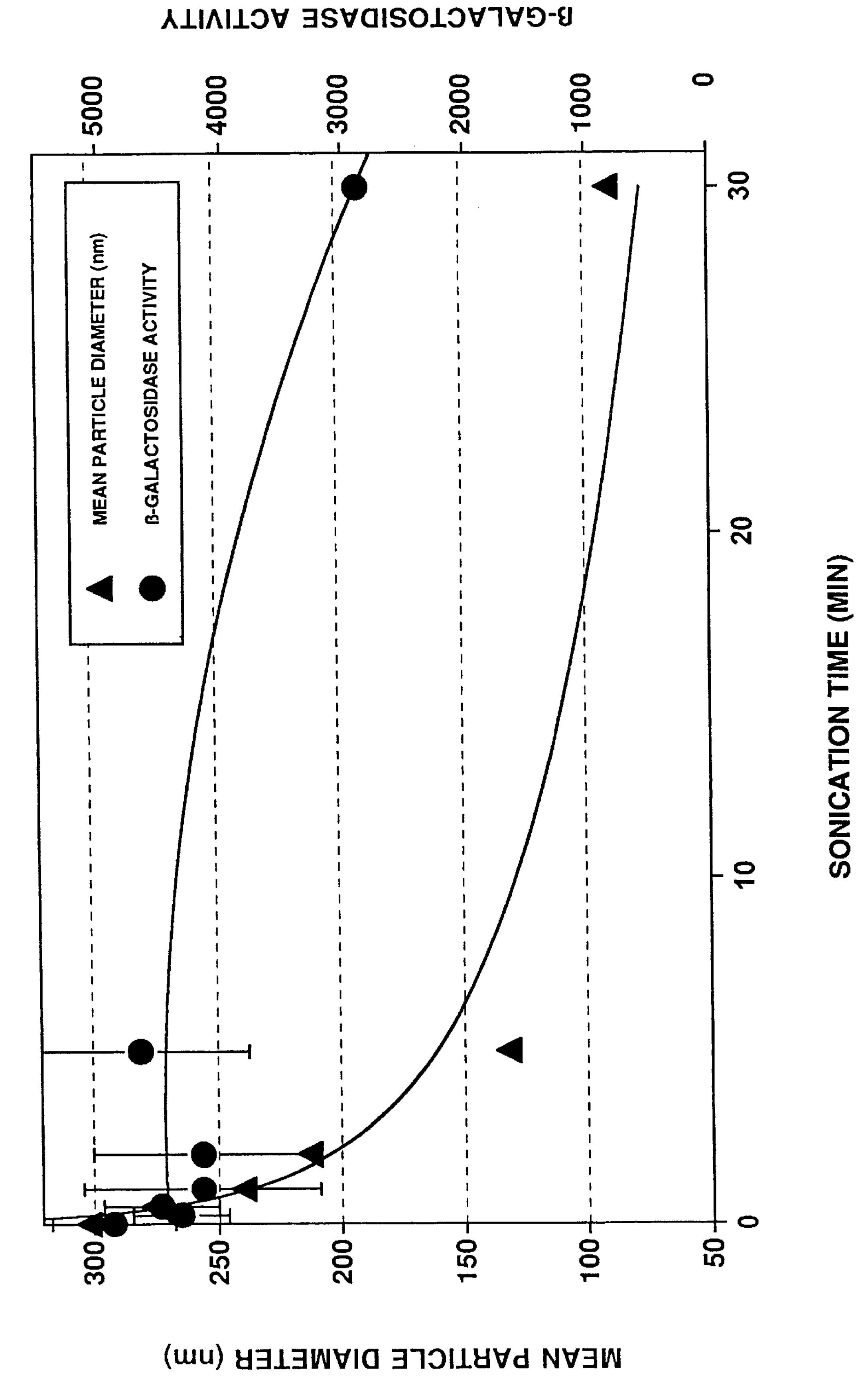
FIG. 6 shows effects of sonication of lipid on particle size and transfection of A549 cells with BGTC:DOPE:pCMVβ. BGTC:DOPE (1:1) was formulated. The lipid was subjected to sonication and aliquots were taken at timed intervals indicated for particle size analysis and determination of transfection efficiency. pCMVβ plasmid DNA was complexed with the lipid samples after sonication. A constant concentration of DNA was used throughout the experiment. A549 cells were transfected for 6 hours and were harvested and extracted for β-galactosidase analysis 48 hours after initiating transfection. Levels of β-galactosidase activity for time points out to 5 minutes were not significantly different from 0 minutes. Activity at 30 min was significantly lower than the 0 minutes control (p<0.05, paired t-test, n=3). The particle size distribution was determined for each time point by Nicomp light scattering analysis and presented as density-weighted mean particle diameter.

Due to the above findings in FIGS. 5A–5C for DL-EPC:DOPE, the relationship between BGTC:DOPE:DNA complex size and transfection using prior sonication was examined as a means of particle size modification. FIG. 6 shows β-galactosidase activity following no sonication or increasing periods of sonication of BGTC:DOPE formulations up to 30 minutes. As with DL-EPC above, somewhat better results were noted when the preparation was not sonicated. However, unlike DL-EPC:DOPE:DNA complexes, there was no decrease in activity of BGTC:DOPE:pCMVβ complexes with increasing sonication out to 5 min. At 30 minutes there was a moderate reduction in β-galactosidase activity.

FIG. 6 also shows the particle size (mean diameter) of BGTC:DOPE-pCMVβ complexes resulting from complexing DNA with lipid components sonicated for the times indicated. Particle size of the lipid components reduces quickly with sonication and comparison of the two curves reveals that transfection activity for BGTC:DOPE:DNA falls more slowly than particle size. There was no major reduction in transfection until the particle size dropped below about 125 nM. Even at a particle size range of 50–100 nm, the complexes still retained 60–70% of the transfection activity exhibited by the unsonicated preparations.

EXAMPLE 18

Figure 7:
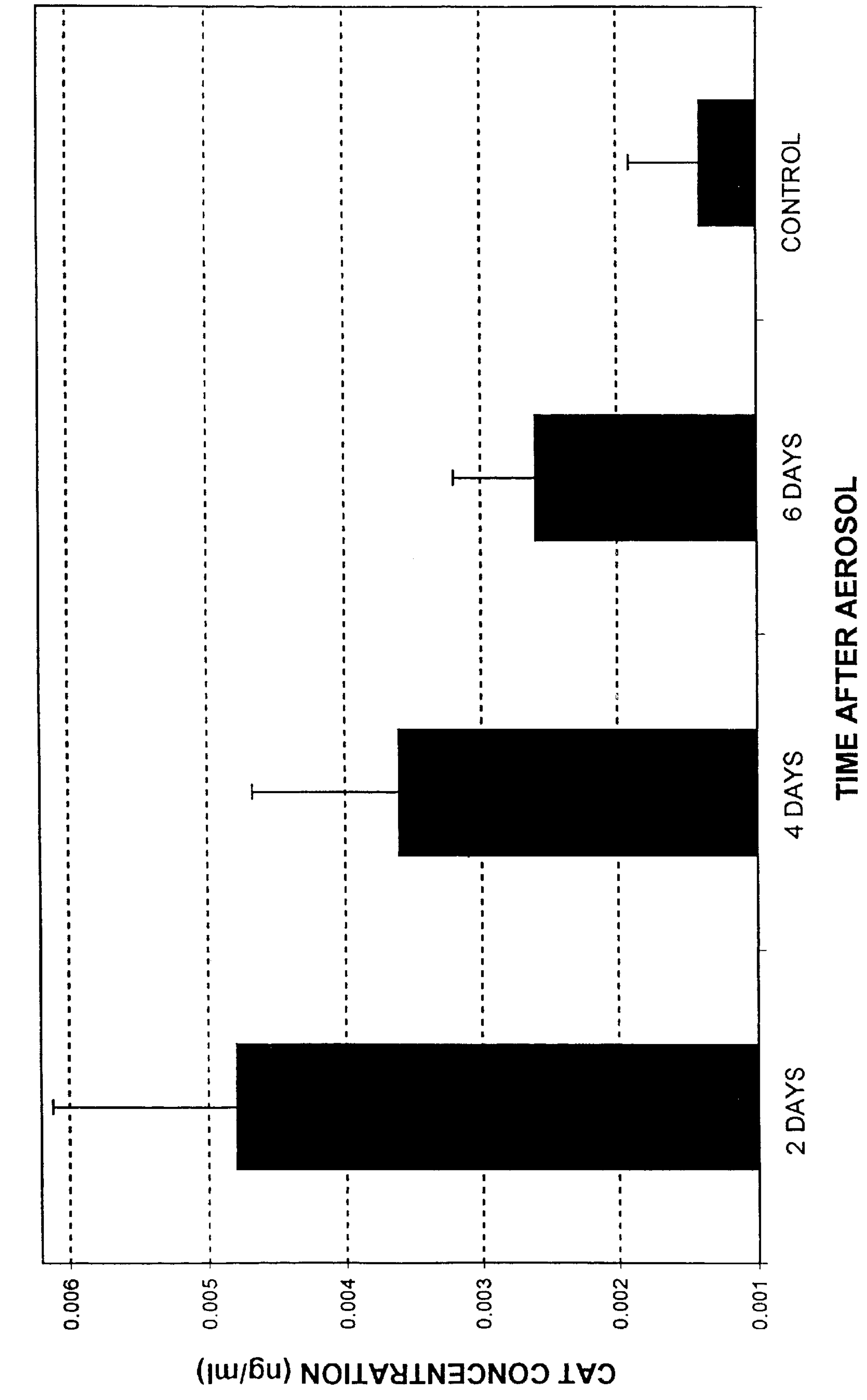
FIG. 7 shows persistence of CAT expression in mouse lungs after aerosol delivery of BGTC:DOPE:pCMVβ. BGTC:DOPE:pCMVHiCAT (2.5:2.5:1) was formulated. Balb-c mice were exposed to aerosolized lipid:DNA formulation overnight and a total of 2 mg of plasmid DNA was delivered. Animals were sacrificed and tissues removed at time intervals indicated following the initiation of the aerosol exposure. Lungs were extracted and analyzed for CAT activity. CAT activity is expressed as the concentration per ml of tissue extract obtained. Values for Day 2 are significantly different from control (P<0.05, paired t-test, n=6).
Figure 8:
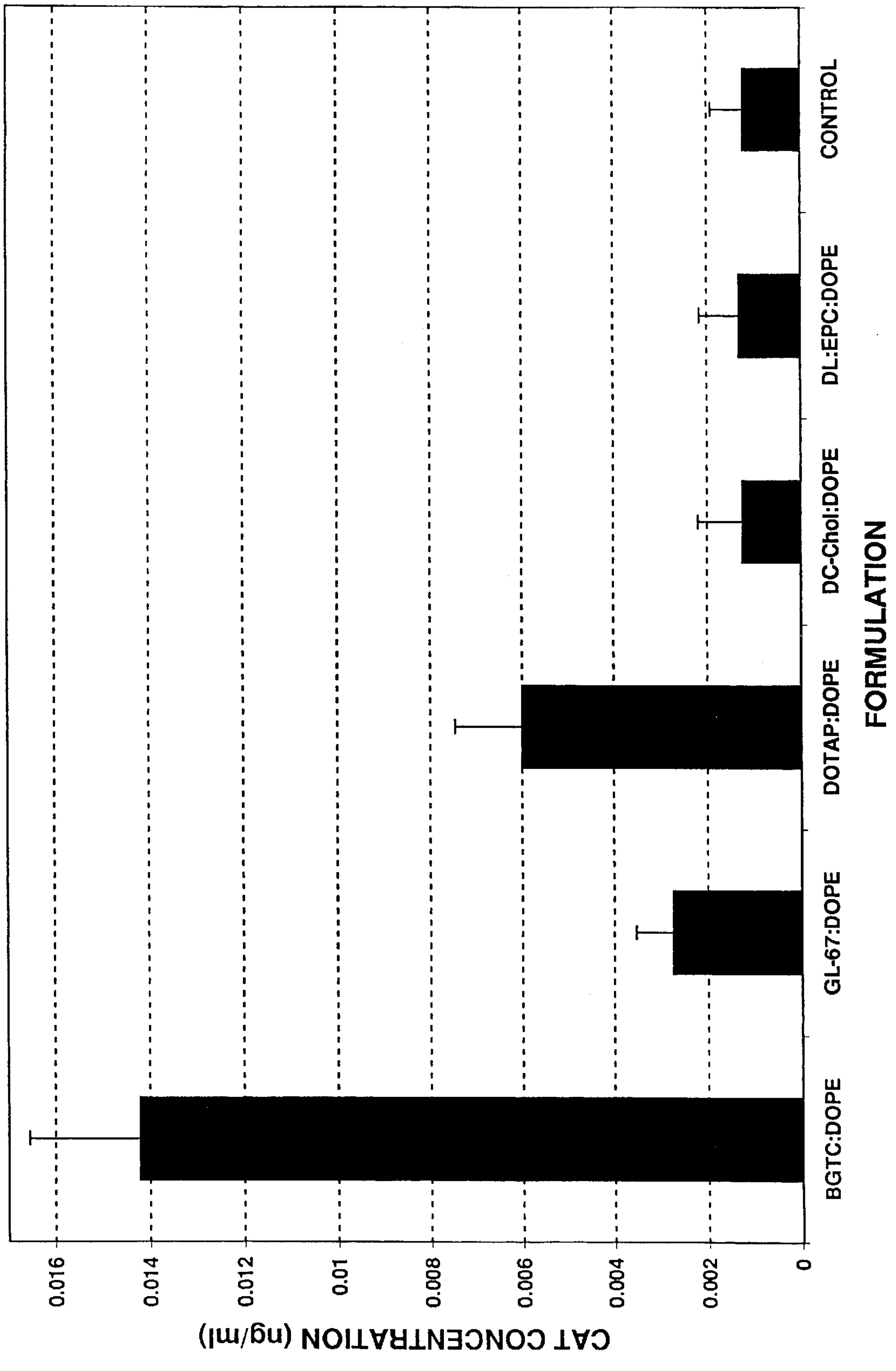
FIG. 8 shows CAT expression in mouse lungs after aerosol delivery of various lipid:DNA preparations. BGTC-:DOPE:pCMVHiCAT (2.5:2.5:1), GL-67:DOPE:pCMVHiCAT (2:4:1), DC-cholesterol:DOPE:pCMVHiCAT (2:2:1), DOTAP-:DOPE:pCMVHiCAT (2.5:2.5:1) and DL-EPC:DOPE:pCMVHiCAT (3:3:1) was formulated. Balb-c were exposed to aerosolized lipid:DNA formulation overnight and animals were sacrificed and tissues removed at 48 hours following the initiation of the aerosol exposure. The amount of DNA delivered to each group of animals (2 mg) was the same. Lungs were extracted and analyzed for CAT activity. CAT activity is expressed as the concentration per ml of tissue extract obtained. Values for BGTC:DOPE are significantly different from all other values (P<0.05, paired t-test for DOTAP:DOPE; P<0.01, paired t-test for GL-67, n=8).

Measurement of pCMVHiCat Gene Activity Recovered from Lungs of Mice Following Nebulization of Liposome-DNA Complexes In vivo transfection in mouse lungs following 10 minutes of nebulization with BGTC:DOPE:pCMVHiCAT is shown in FIG. 7. The lipid:DNA ratio found to be optimal in vivo was slightly higher than that found to be optimal in vitro and the difference in in vivo expression obtained using a 20:80 and 50:50 ratio of BGTC to DOPE was found to be negligible, so a 2.5:2.5:1 ratio by weight of BGTC:DOPE:pCMVHiCAT (2.3:1 ratio of BGTC guanidinium:DNA phosphate) was used for this study. The lungs were examined 2, 4 and 6 days after exposure. Transfecting activity is greatest at 2 days and is progressively reduced thereafter. A comparison of CAT gene activity was made following nebulization of BGTC:DOPE:pCMVHiCAT (2.5:2.5:1), GL-67:DOPE:pCMVHiCAT (2:4:1), DC-cholesterol:DOPE:pCMVHiCAT (2:2:1), DOTAP:DOPE:pCMVHiCAT (2.5:2.5:1) and DL-EPC:DOPE:pCMVHiCAT (3:3:1) into mouse lungs (FIG. 8). The lungs were studied two days after nebulization.

The CAT activity of the BGTC:DOPE preparation was about 2.4-fold greater than that with the DOTAP:DOPE preparation and about 7-fold greater than that with the GL-67:DOPE preparation, which was only slightly greater than the control. DC-cholesterol:DOPE:pCMVHiCAT and DL-EPC:DOPE:pCMVHiCAT proved to be ineffective under in vivo aerosol conditions. Different formulations (lipid:co-lipid:DNA ratios) were used for the different lipids based on what had been determined to be optimal for each lipid.

EXAMPLE 19

Electron Microscopic Studies of Liposome-DNA Complexes

One of the purposes of the study was to visualize the effect of nebulization on the morphology of the liposome-DNA complexes in material recovered from the reservoir of the nebulizer or from samples of aerosol collected by impinger. Another purpose was to observe the effect of co-lipids on liposome-DNA complex morphology.

Figure 9A:
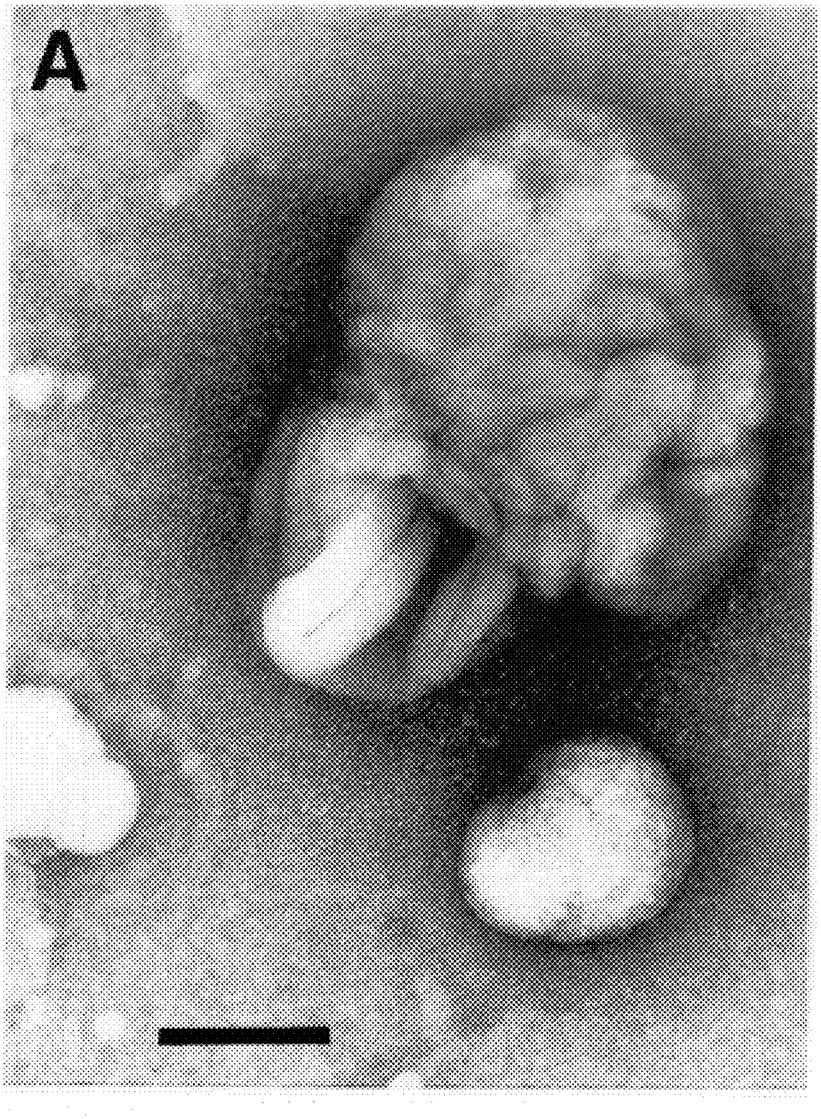
FIGS. 9A–9D shows the effect of nebulization on the ultramicroscopic morphology of BGTC:DOPE:pCMVβ liposome complexes by negative staining and cryofixation. BGTC:DOPE:pCMVβ (1.5:1.5:1) was formulated. An aliquot was taken prior to nebulization (FIG. 9A), another was taken from the nebulizer reservoir after 6 minutes of nebulization at 8 L/min (FIG. 9B) and a sample of aerosol was collected by AGI from 0 to 3 minutes during the nebulization process (FIG. 9C). A postnebulization sample (same as FIG. 9B) is examined by cryofixation and sectioning (FIG. 9D). Aliquots were simultaneously collected for particle size analysis. All samples were examined by the uranyl acetate negative staining procedure. Bars on all micrographs represent 100 nm.

Prior to nebulization, samples of liposome-DNA (BGTC:DOPE:pCMVβ at 1.5:1.5:1 by weight (1.4:1 by BGTC guanidinium:DNA phosphate)) were composed of heterogeneously sized and shaped particles as examined by negative staining (FIG. 9A). Particle sizes range from several microns in diameter down to a few nanometers. A preparation recovered from the reservoir after 6 minutes of nebulization (FIG. 9B) shows irregularly shaped liposomes (100 to 300 nm) like the large particles seen in FIG. 9A. A new feature of the post nebulization sample (FIG. 9B) was the presence of fine, worm-like structures which appear to be short lengths of lipid bilayers that have been separated from the larger structures in FIG. 9A. These structures were seen in other post-nebulization preparations. FIG. 9C shows material recovered from aerosol (collected by the AGI-4 impinger). A typical particle with a diameter of about 175 nm is shown. FIG. 9D shows the post nebulization sample (same as FIG. 9B) examined by cryofixation and sectioning. This image reveals that the preparation clearly retains its multilamellar structure during the nebulization process.

Figure 9B:
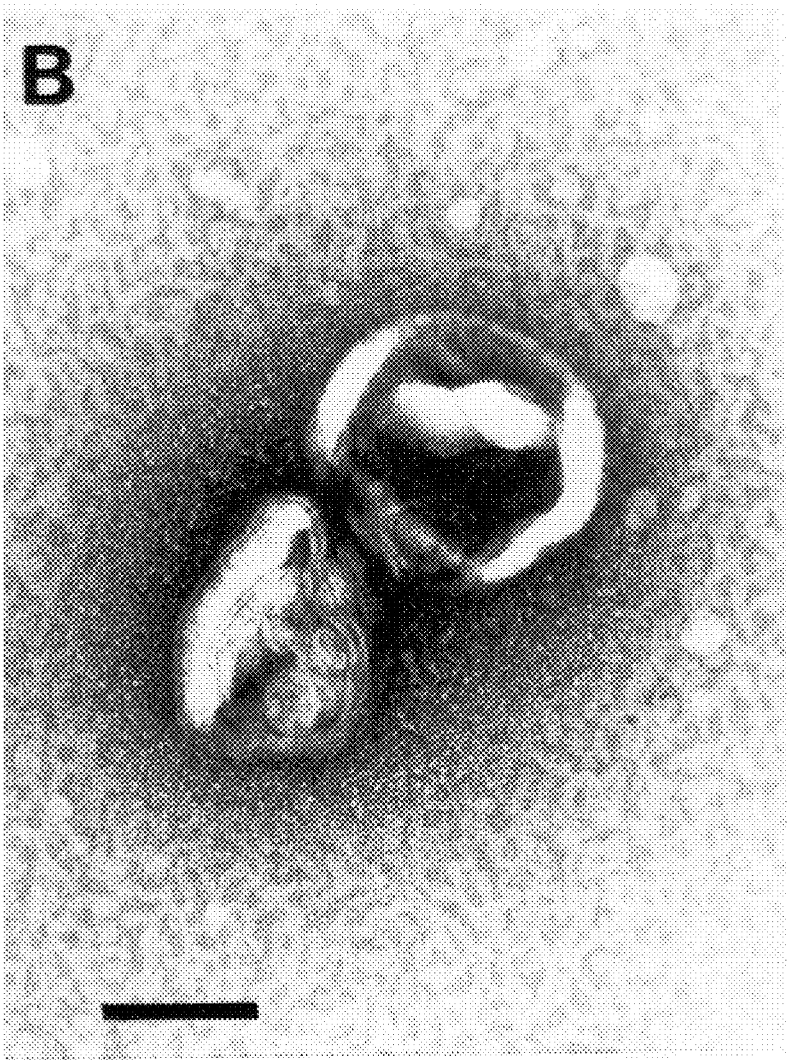
Figure 9C:
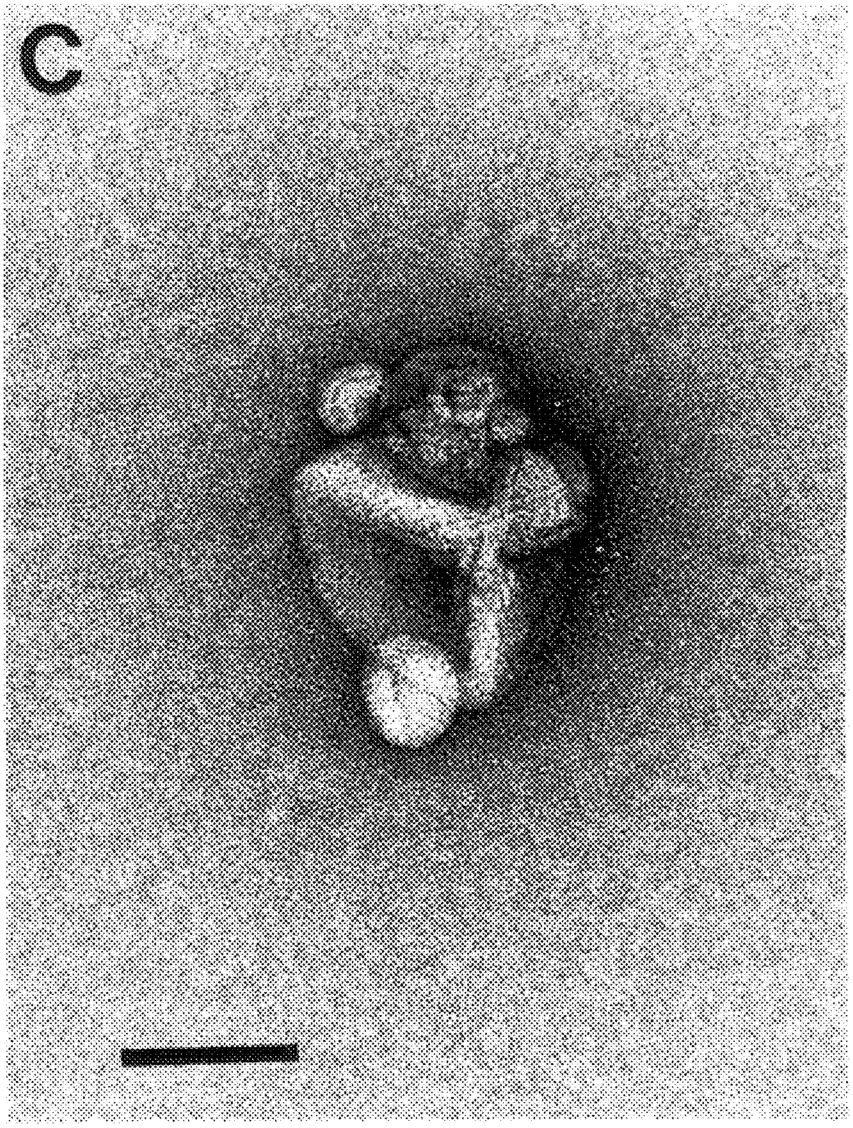
Figure 9D:
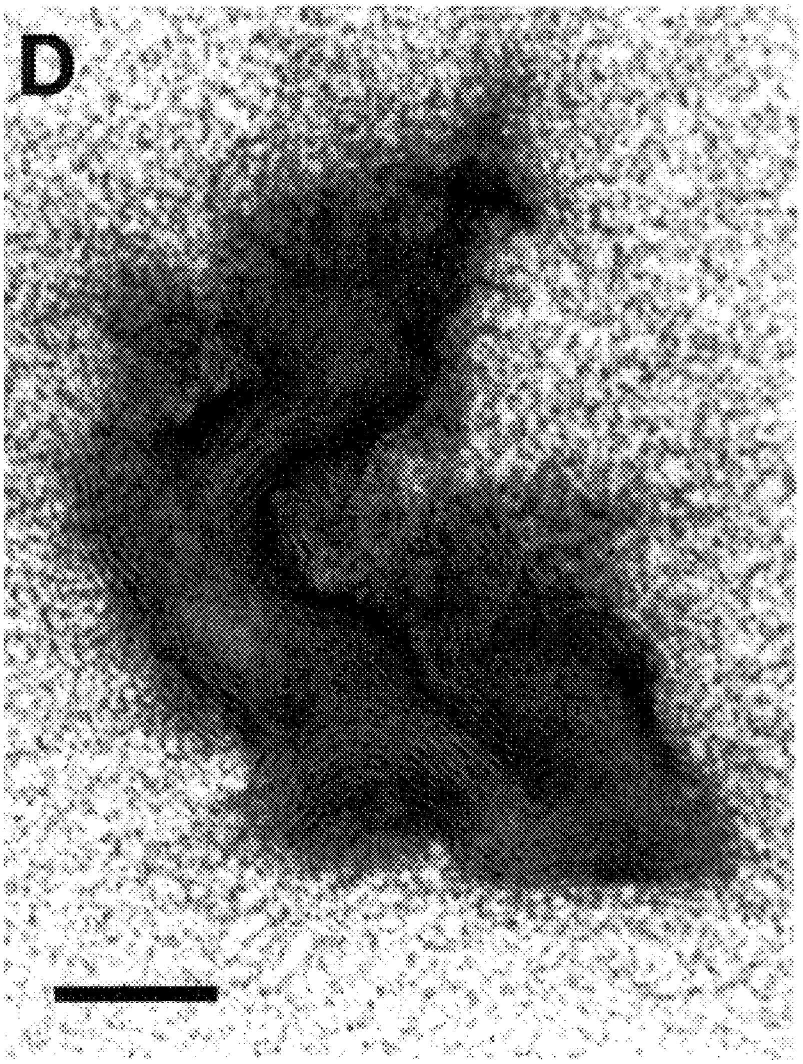

Preparations obtained from the nebulizer before and after nebulization, matching material in FIGS. 9A and 9B were examined in the Nicomp laser particle analyzer. The mean size of particles before nebulization was 621 nm with peaks of 34.9 nm, 262.2 nm and 1134.7 nm, indicative of a wide range of sizes of the particles. After nebulization for 0–3 minutes, the mean particle size was 271.8 nm with peaks of 81.7 nm and 278.8 nm. Other studies are consistent with these results. Further nebulization does not further reduce the size; apparently this size is representative of the maximum effect of the aperture of the nebulizer and other properties of the nebulizer function on the particles.

Figure 10A:
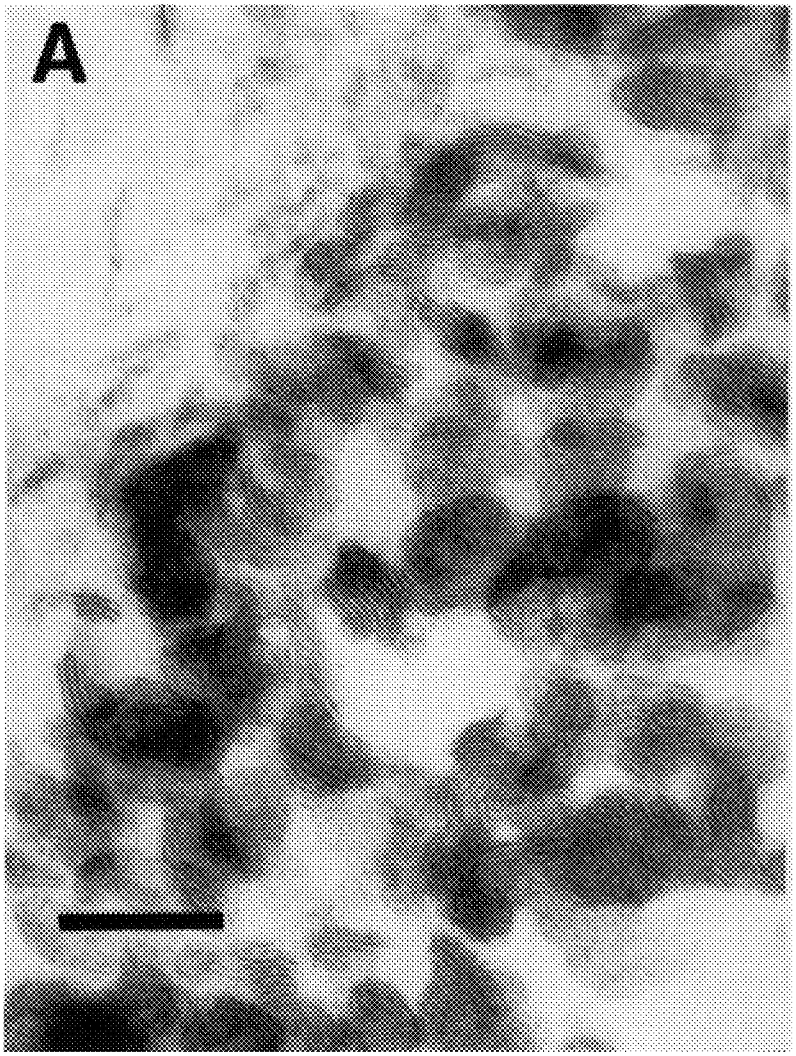
FIGS. 10A–10D shows the effect of DOPE on the ultramicroscopic morphology of BGTC:DNA liposomal morphology. BGTC or BGTC:DOPE was formulated and complexed with pCMVβ. These samples without DOPE were prepared using a BGTC:DNA ratio of 3:1 (FIG. 10A) or with DOPE using a 1.5:1.5:1 ratio of the three components before (FIG. 10B) or after (FIG. 10C) nebulization. For comparison, a preparation of BGTC:DOPE:pCMVβ (0.6:2.4:1 by weight) is shown wherein the proportion of DOPE has been further increased to 80% of the total lipid (FIG. 10D, not nebulized). These suspensions were osmium fixed prior to centrifugation, embedding and sectioning. These images represent thin sections (approx. 60 nm) stained with uranyl acetate and lead citrate. Bars on all micrographs represent 100 nm.

FIG. 10A shows a preparation of liposome-DNA complexes from which DOPE has been omitted and was prepared by chemical fixation and sectioning. Many small size lamellar structures with sharp and irregular borders are typical. These structures have the appearance of being fragmented from larger structures and numerous small linear pieces are present which appear to be fragments of bilayers. However, this preparation has not been subjected to nebulization or any other physically disruptive process and thus there is not a ready explanation for the apparent small size of the liposome-DNA complexes.

Figure 10B:
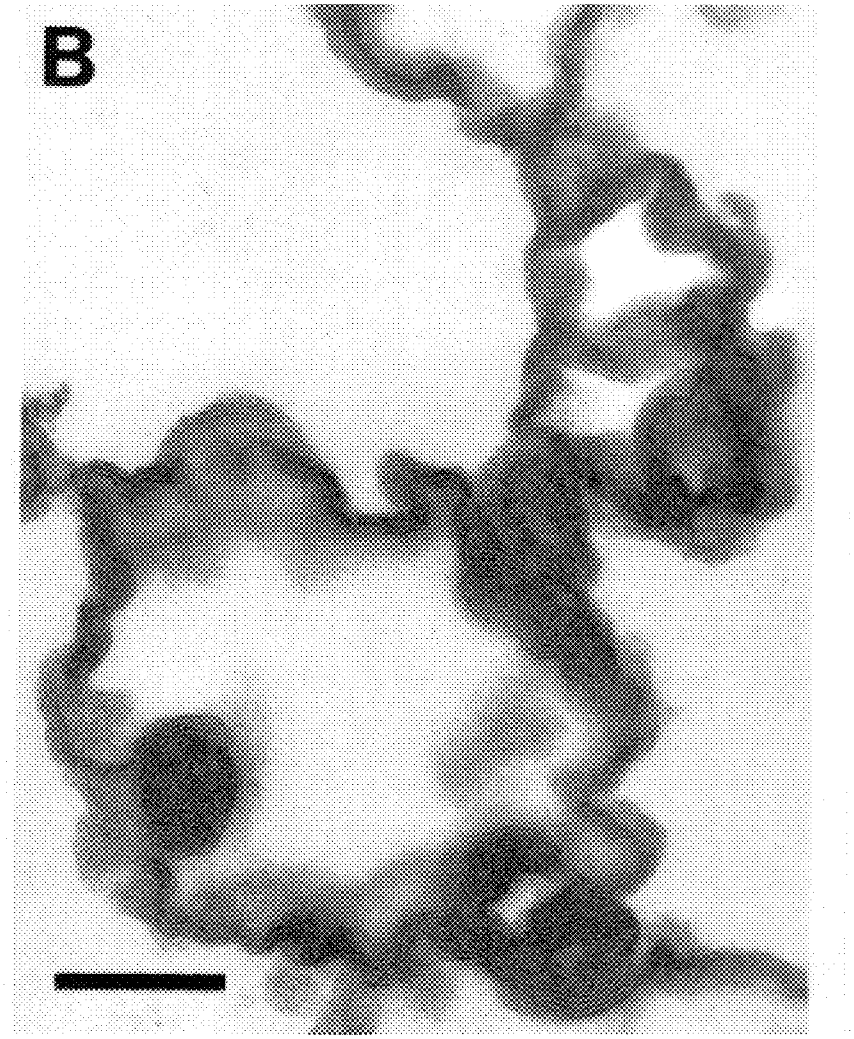
Figure 10C:
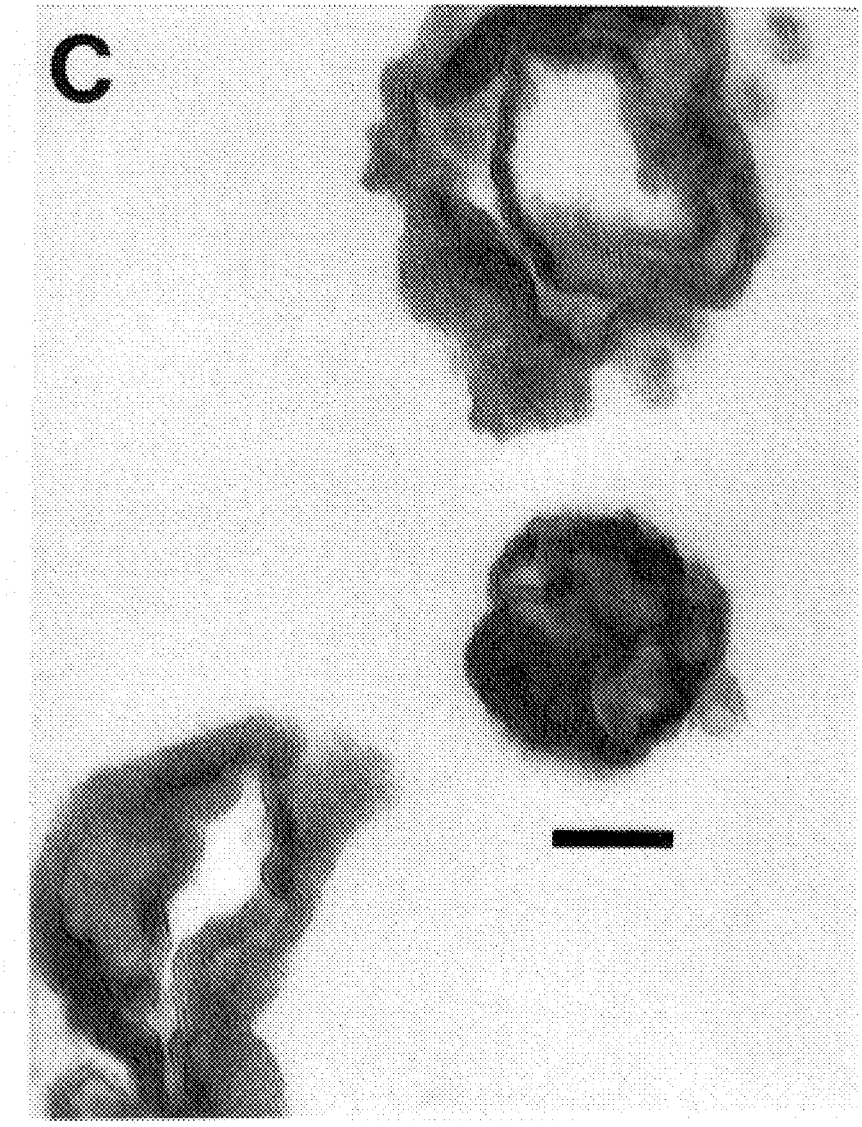
Figure 10D:
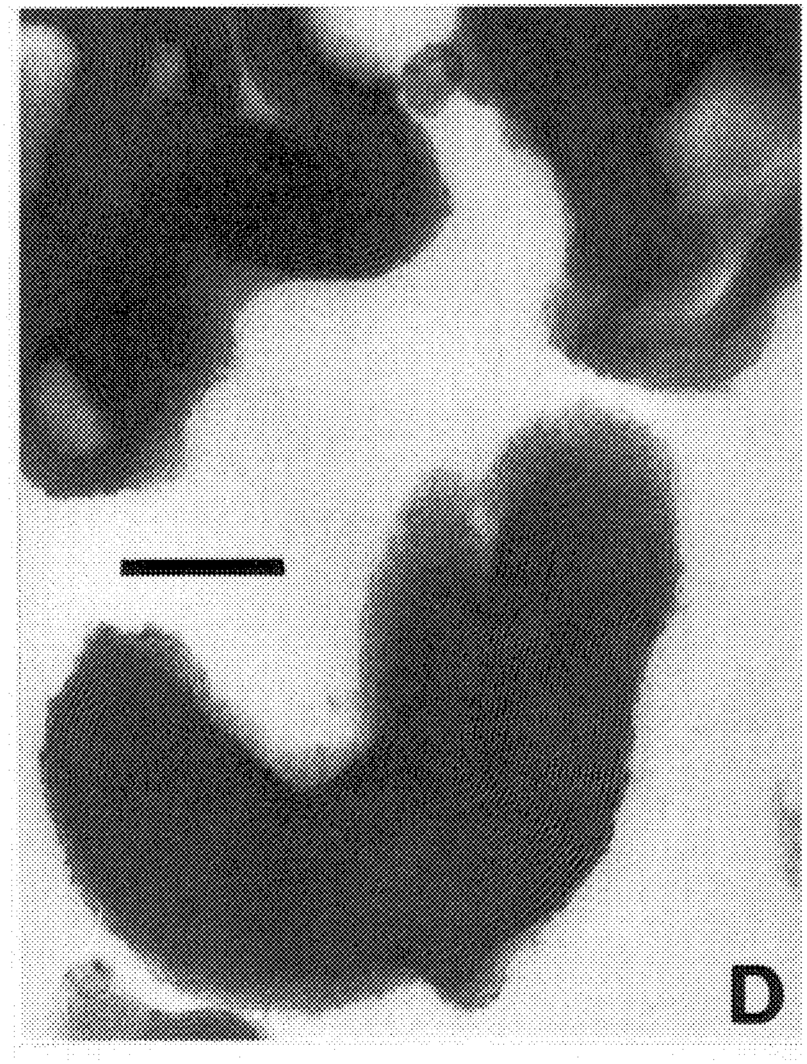

A preparation of BGTC:DOPE:pCMVβ (1.5:1.5:1.5 w:w:w) is shown in FIG. 10B wherein the concentration of DOPE has been restored to 50% of the total lipid. The material has not been nebulized and is the same as that seen in FIG. 9A. The section depicted only shows a portion of a typical unnebulized complex of this formulation. After nebulization for 6 minutes, the BGTC:DOPE:pCMVβ (1.5:1.5:1.5 by weight) preparation (same as FIG. 9B) is exemplified in FIG. 10C by smaller, rounder particles which retain their multilamellar appearance. A preparation of BGTC:DOPE:pCMVβ (0.6:2.4:1 by weight) is shown in FIG. 10D wherein the proportion of DOPE has been further increased to 80% of the total lipid. Although this preparation was not nebulized, the overall size of the particles was quite uniform ranging form 300 to 500 nm.

EXAMPLE 20

Additions of Certain Constituents to the Liposome-DNA Complexes

Figure 11:
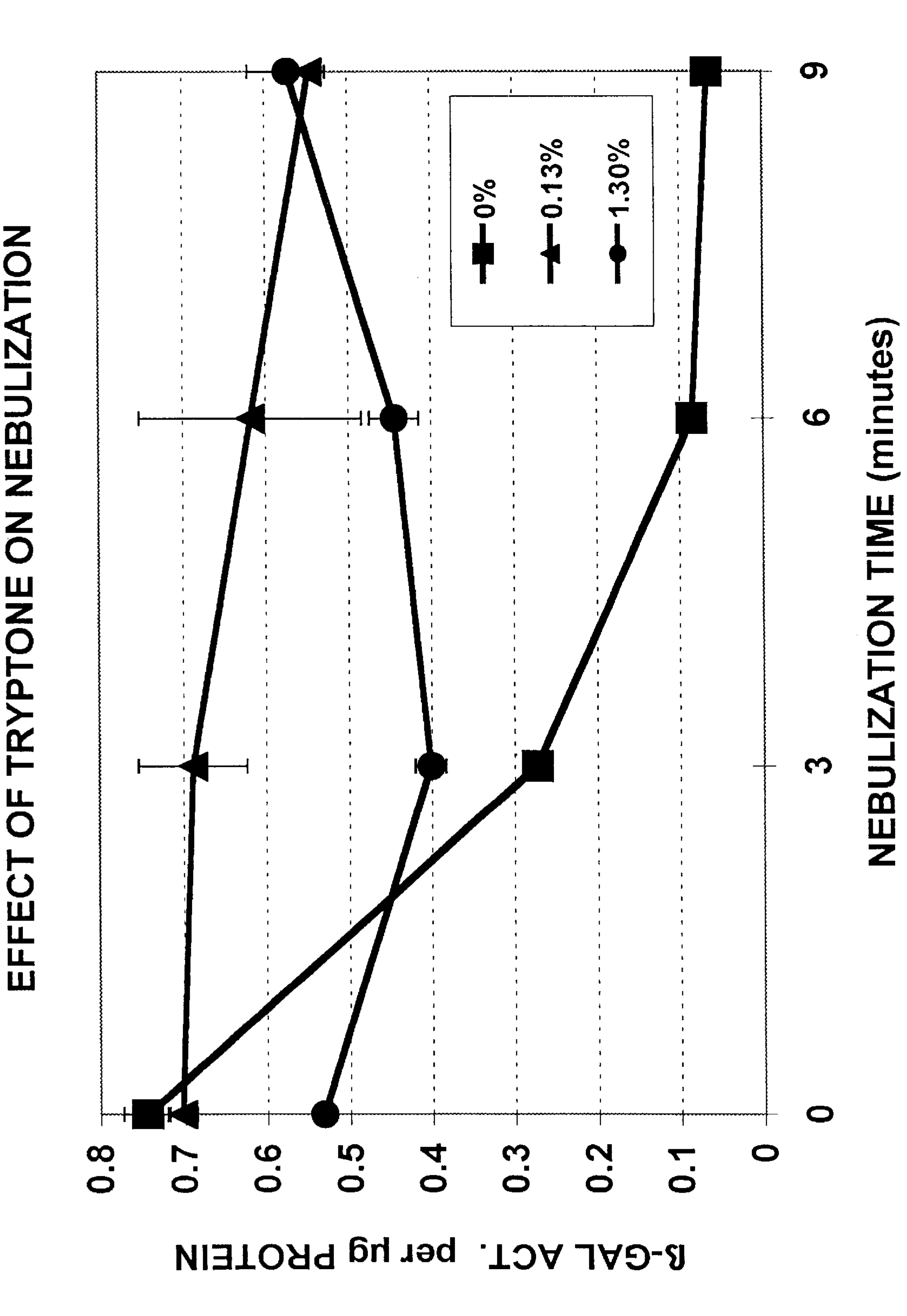
FIG. 11 shows that the addition of 1.3% tryptone to the nebulizer solution produced a similar, but intermediate, level of protection against nebulizer-induced losses.

Certain constituents, when added to the lipid:DNA suspension prior to nebulization, stabilized the transfection potential of these formulations significantly. This results in a many-fold increase in the quantity of biologically active gene therapeutic agent being delivered. Over several experiments, the addition of 0.13% tryptone, an enzymatic (tryptic) digest of casein, to the nebulizer solution resulted in 105%, 100% and 93% retention of the transfection activity of the control (unnebulized) material in an in vitro assay using A549 human lung tumor cells when aliquots of the nebulizer-cycled material were removed from the nebulizer reservoir at 3, 6 and 9 minutes of nebulization respectively at a flow rate of 15 L/min and a starting volume of 5 ml. This compares to a 51%, 13% and 6% retention of transfection activity for the control (no tryptone added). An addition of 1.3% tryptone produced a similar, but intermediate, level of protection against nebulizer-induced losses (see FIG. 11).

These results were obtained for a formulation consisting of DL-EPC/DOPE complexed with pCMVβ-GAL plasmid DNA (for the expression of β-galactosidase). Similar stabilization of transfection activity was achieved when this experiment was repeated twice more. The nebulizer used was a modified Puritan Bennett 1600 nebulizer (Carlsbad, Calif.)—one tube from the twin jets was removed—this nebulizer is referred to as the Puritan Bennett 1600 single jet (PB sj). The control nebulizer solution consisted of 200 μg of pCMVβ-GAL and 700 μg of DL-EPC/DOPE complexed in Water for Irrigation (WFI; Baxter) in a total volume of 5 mls. The nebulizer solution with 0.13% tryptone contained the same amount of plasmid DNA and lipid. A 50 μl aliquot of a 13% tryptone stock solution (13% w/v in WFI) was added to the nebulizer solution after the DNA and lipid had complexed for 15 minutes (the final volume remained at 5 mls). The nebulizer solution with 1.3% tryptone also contained the same amount of plasmid DNA and lipid. A 0.5 ml aliquot of a 13% tryptone stock solution (13% w/v in WFI) was added to the nebulizer solution after the DNA and lipid had complexed for 15 minutes (the final volume after the addition of the tryptone was 5 mls).

Figure 12:
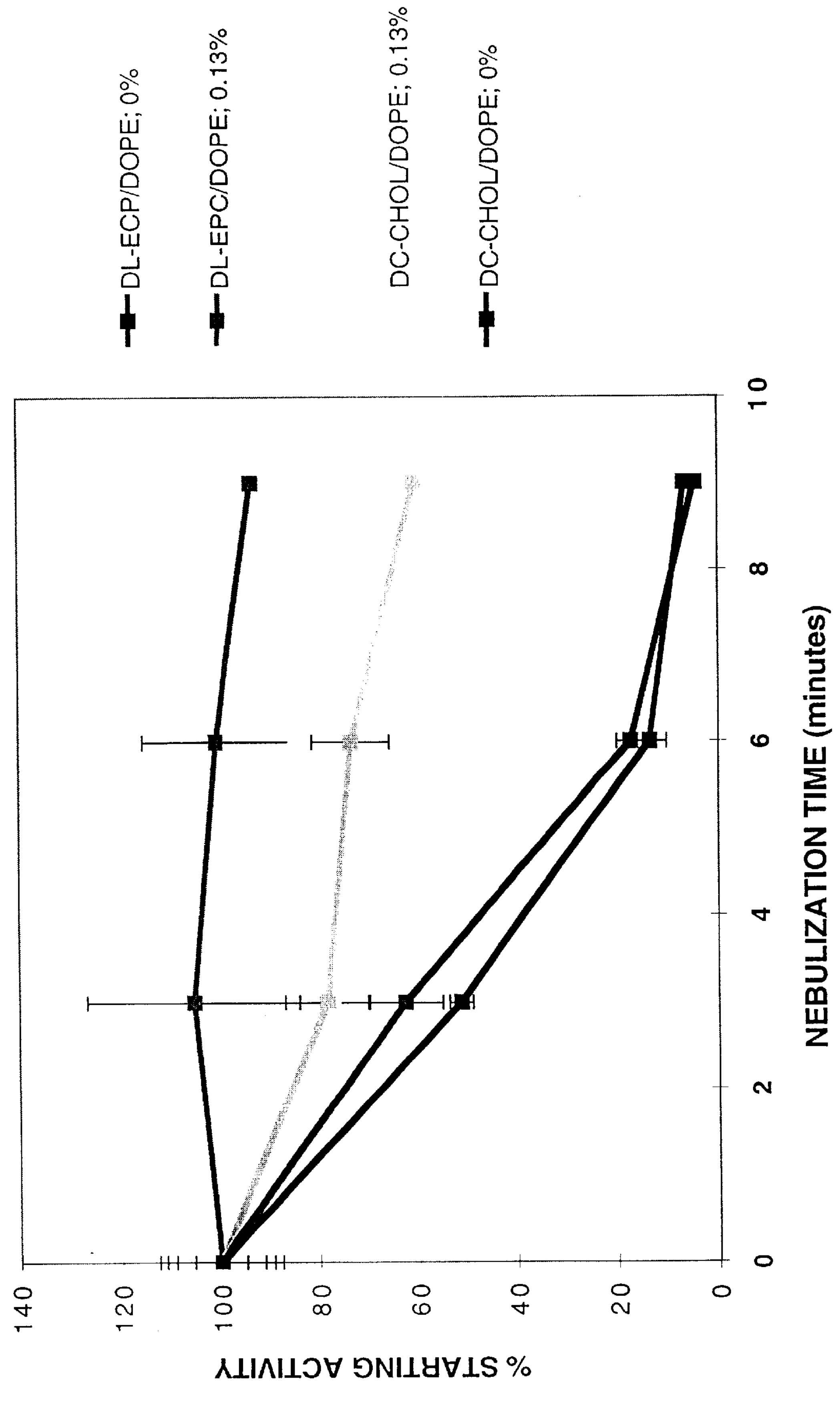
FIG. 12 shows a comparison of the effects of tryptone on the nebulizer-induced losses encountered with different lipids.

In addition, a similar stabilization was achieved when using a formulation consisting of DC-CHOL/DOPE and pCMVβ-GAL, indicating that the effect is apparently not dependent upon a specific cationic lipid for lipid formulation. The control nebulizer solution consisted of 200 μg of pCMVβ-GAL and 800 μg of DC-CHOL/DOPE complexed in WFI in a total volume of 5 mls. The nebulizer solution with 0.13% tryptone contained the same amount of plasmid DNA and lipid. A 50 μl aliquot of a 13% tryptone stock solution (13% w/v in WFI) was added to the nebulizer solution after the DNA and lipid had complexed for 15 minutes (the final volume remained at 5 mls). The nebulizer solution with 1.3% tryptone also contained the same amount of plasmid DNA and lipid. A 0.5 ml aliquot of a 13% tryptone stock solution (13% w/v in WFI) was added to the nebulizer solution after the DNA and lipid had complexed for 15 minutes (the final volume after the addition of the tryptone was 5 mls). A comparison of the effects of tryptone on the nebulizer-induced losses encountered with both lipids is illustrated in FIG. 12.

Figure 13:
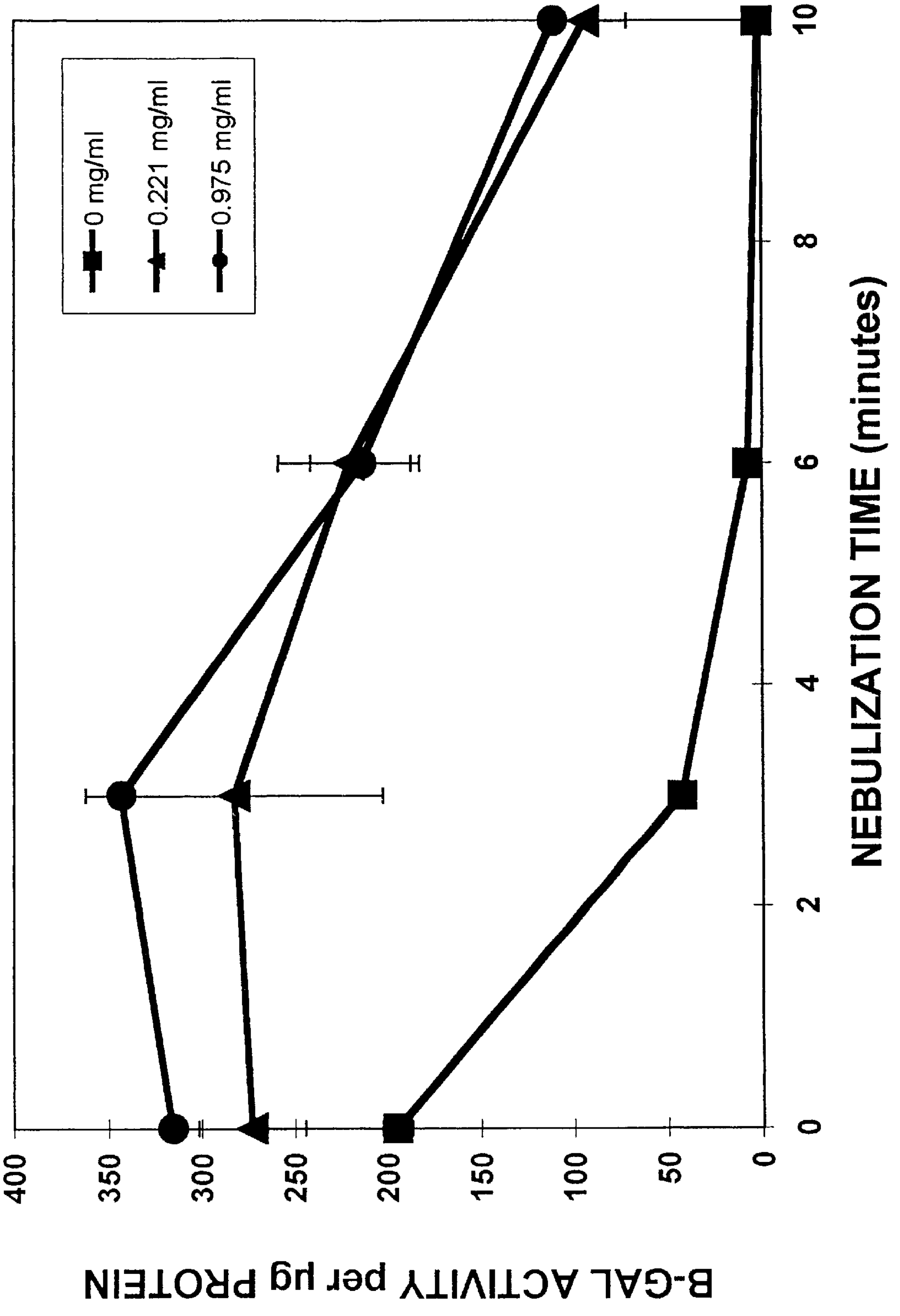
FIG. 13 shows that glutamic acid also provided a significant degree of protection against nebulizer-induced loss of cell transfection activity when present at concentrations equivalent to the concentrations in tryptone.

Since tryptone is composed of a number of components, whether one or more specific components was responsible for the observed aerosol stability was examined. Glutamic acid, a major amino acid component of tryptone, also provided a significant degree of protection against nebulizer-induced loss of cell transfection activity when present at concentrations equivalent to the concentrations that would have been present in the concentration of tryptone found effective in the above experiments (see FIG. 13). This experiment was conducted in the same fashion as the previously described experiments using DC-cholesterol:DOPE:pCMVβ-GAL and glutamic acid in the concentrations of 0.221 mg/ml and 0.975 mg/ml and has also been replicated. The control nebulizer solution consisted of 200 μg of pCMVβ-GAL and 800 μg of DC-Chol/DOPE complexed WFI in a total volume of 5 mls. The nebulizer solution containing 0.221 mg/ml glutamic acid also contained the same amount of plasmid DNA and lipid.

A 0.227 ml aliquot of a 4.875 mg/ml glutamic acid stock solution (in WFI) was added to the nebulizer solution after the DNA and lipid had complexed for 15 minutes (the final volume after the addition of the glutamic acid was 5 mls). The nebulizer solution containing 0.975 mg/ml glutamic acid also contained the same amount of plasmid DNA and lipid. A 1 ml aliquot of a 4.875 mg/ml glutamic acid stock solution (in WFI) was added to the nebulizer solution after the DNA and lipid had complexed for 15 minutes (the final volume after the addition of the glutamic acid was 5 mls).

Discussion

The present invention reports that BGTC:DOPE liposome-DNA complexes substantially resisted degradation (based on in vitro functional stability) associated with aerosolization by jet nebulization. In vivo transfection also occurred in the lungs of mice following aerosol exposure to BGTC:DOPE liposome-DNA complexes and compared favorably to several extensively studied cationic lipids. Co-lipids play an important role in both the in vitro transfection efficiency and the aerosol delivery efficiency with formulations consisting of 50% to 80% DOPE (by weight of the lipid component) resulting in stable preparations that were efficient both in vitro and in vivo. Interestingly, it was found that preparations of lipid:DNA that were optimal for transfection in vitro had charge ratios in the 0.5:1 to 1:1 (BGTC guanidinium:DNA phosphate) range when the relative concentration of the neutral co-lipid DOPE was high. This is less than that predicted from the findings of Vigneron et al. (11). It thus appears that transfection is a complex process influenced by charge ratio, co-lipid composition, particle size and a variety of other factors.

Clearly, the efficient aerosol delivery of liposome-DNA complexes to the lungs and airways requires careful attention to a number of factors related to nebulization and some of these have previously been evaluated (1, 19–20). The choice of nebulizer is important since the aerosol droplet size and concentration of liposome-DNA complexes in the aerosol determine the pattern of pulmonary deposition and dose. Puritan Bennett sj nebulizer was chosen based on an output with a mass median aerodynamic diameter of about 1.5 microns, ideal for optimal deposition in the lower airways and alveolar regions of the lungs. The optimization of liposome-DNA formulation has also been the focus of study in recent years (7, 9, 11–13, 21) since it is evident that formulations ideal for other modes of in vivo gene delivery (i.e., i.v.) are not necessarily optimal for transfection of respiratory epithelial cells by aerosol and issues such as toxicity (22) and clearance must be taken into account.

It is evident from these studies that stability of formulations during small particle aerosol nebulization appears to be influenced not only by the choice of cationic lipid, but also by the choice of co-lipid, the cationic lipid:co-lipid ratio and the DNA:lipid ratio. While some lipids have been reportedly stabilized by the addition of additional reagents such as polyethylene glycol-containing lipids (21), the finding that BGTC:DOPE formulations are stable during nebulization in the absence of these reagents could have important implications for clinical applications of aerosol gene delivery.

BGTC:DOPE formulations were subjected to sonication in order to examine the effects of liposome-DNA complex particle size on transfection efficiency. Nebulization has been shown in this study to reduce the mean liposome-DNA particle size, yet the findings with variably sized particles resulting from sonication (FIG. 5B) indicate that nebulization does not result in enough reduction in size to impact significantly the transfection efficiency of aerosol-delivered BGTC:DOPE:DNA particles. The finding of a more pronounced association between reduced particle size and lower transfection efficiency, both in vitro and in vivo, with liposome-DNA formulations prepared with other cationic lipids such as DL-EPC:DOPE may partially explain why many lipids are less stable than BGTC:DOPE during the nebulization process.

The results of radioisotope uptake experiments using sonicated and unsonicated DL-EPC formulations suggests that the effects of size on transfection efficiency in vitro may not be entirely due to the increased sedimentation of the larger particles. This finding also appears to be reflected in the higher level of transfection of pulmonary sites in vivo resulting from the instillation of unsonicated preparations containing larger particles. The notion that larger liposome-DNA particle size may be favorable in some in vivo applications has been reported by other workers. One group (23) using extruded DOTAP:cholesterol liposomes found that systemic gene expression was optimal with liposome-DNA complexes of 200 to 450 nm (compared with particles of less than 200 nm).

The findings for BGTC:DOPE as well as the other lipids examined here regarding the effects of lipid:DNA complex size on transfection efficiency in vitro and in vivo could have implications for the methods of lipid:DNA preparation for various clinical applications. The process of nebulization is, in effect, an extrusion process since all of the material must pass repeatedly through a very small aperture (much less than 0.1% cent of liquid nebulized at any one time is discharged as aerosol). However, the resulting particle size is larger than that obtained when lipids were sonicated for extended periods of time (i.e. 30 min). Even with BGTC:DOPE formulations, sonication for 30 min was associated with a decrease in transfection efficiency. It should be emphasized that the size of the aqueous droplets carrying the liposome particles is the determining factor in the site of deposition in the respiratory tract. The reduction in particle size of liposomes resulting from continuous passage through the nebulizer to a few hundred nanometers in diameter simplifies the preparation and use of liposomes in aerosol. This may eliminate the need for sonication during formulation preparation and reduce concerns about liposome-DNA complex aggregation during the shelf life of formulations destined for clinical applications.

Several recent studies have examined cationic lipid:DNA complex morphology at the electron microscopic level (24–27) and some of these findings have contributed to current hypotheses regarding structural correlates of lipid-mediated transfection. The preparation of BGTC:DOPE:p-CMVβ (0.6:2.4:1 by weight) containing the highest percentage of DOPE, showed denser, distinctly lamellated and more uniform, small-sized liposome-DNA aggregates than those with a smaller proportion of DOPE, and these liposomes transfected more efficiently than those with the smaller proportion of DOPE. While it is possible that the BGTC:DOPE:DNA complexes examined in the present study exist partially in the inverted hexagonal form described for other cationic lipid:co-lipid:DNA formulations by Koltover et al. using synchrotron x-ray diffraction (28), and by Sternberg et al. (26) using cryo-transmission electron microscopy as the transfectionally active form, it appears that the predominant morphology for transfectionally active BGTC:DOPE formulations is multilamellar. Further definition of structure was not possible with these methods.

It should be noted that almost any method of fixation or staining used to visualize liposomes by electron microscopy may be associated with artifactual changes in liposomal morphology, including changes in shape or aggregation of particles. Even freeze fracture methods can be associated with artifacts since simple plunge freezing usually results in the formation of ice crystals that push suspended particles into gaps between the ice called eutectics. While ice crystal formation can be minimized by cryoprotectants such as glycerol, these reagents can also destabilize lipids. For these reasons, the current study employed several different methods for ultrastructural visualization.

Multilamellar or 'liposomal' morphology of BGTC:DOPE formulations revealed by conventional negative staining and chemical fixation procedures in this study was confirmed by a cryofixation method that employs a high pressure freezing step followed by fixation and dehydration at subfreezing temperatures to eliminate the formation of ice crystals. It also helped to confirm that this structure was well maintained during the repeated extrusion of this material through the aperture of a nebulizer jet. The worm-like structures evident in negatively stained preparations of nebulized material are somewhat reminiscent of the bilayer-covered DNA tubules (spaghetti) originally described by Sternberg et al. (25) for DC-cholesterol:DOPE. However, it is not certain that the structures described in the present invention contain DNA.

Although detailed data regarding the toxicity of BGTC formulations are not presented here, no histological evidence of inflammatory responses were seen in any of the animals exposed to BGTC:DOPE:DNA aerosol in these studies. In addition to the obvious application of such a nebulizer-resistant formulation to the treatment of cystic fibrosis, promising results have been obtained with BGTC-:DOPE:p53 formulations in in vitro studies designed to inhibit or reverse lung tumor growth. The aerosol stability and in vivo effectiveness of these formulations may allow for the effective treatment of lung tumors via a noninvasive approach with low apparent toxicity.

Numerous cationic lipid-based formulations have been shown to be quite labile during the nebulization process and many, as a result, are ineffective as aerosol gene delivery vectors. In contrast, BGTC-based formulations appear to be well suited for aerosol administration and are perhaps even optimized by the shear forces of jet nebulization. These findings have numerous implications for a wide range of clinical applications of lipid-based aerosol gene delivery.

The following references were cited herein.

1. Schwarz et al., *Human Gene Therapy* 1996; 7: 731–741.
2. Crook et al., *Gene Therapy* 1996; 3: 834–839.
3. Feigner et al., *Proc Natl Acad Sci USA* 1987; 84: 7413–7417.
4. Felgner et al., *J Biol Chem* 1994; 269: 2550–2561.
5. Gao et al., *Biochem Biophys Res Comm* 1991; 179: 280–285.
6. Stephan et al., *Human Gene Therapy* 1996; 7: 1803–1812.
7. Lee et al., *Human Gene Therapy* 1996; 7: 1701–1717.
8. Farhood et al., *Biochim Biophys Acta* 1995; 1235: 289–295.
9. Bennett et al., *Bioscience Reports* 1995; 15: 47–56.
10. Fasbender et al., *Gene Therapy* 1997; 4: 716–725.
11. Vigneron et al., *Proc Natl Acad Sci USA* 1996; 93: 9682–9686.
12. Oudrhiri et al., *Proc Natl Acad Sci USA* 1997; 94: 1651–1656.
13. Oudrhiri et al., *Biogenic Amines* 1998; 14: 537–552.
14. May, *Aerosol Science* 1973, 4: 235–243.
15. Waldrep et al., *International Journal of Pharmaceutics* 1993; 97: 205–212.
16. Waldrep et al., *J Aerosol Med* 1994; 7: 135–145.
17. Gilbert B E, Knight V. Pulmonary delivery of antiviral drugs. In *Seminars in Pediatric Infectious Diseases*, Feigin, R. D., and Demmler, G(eds),Philadelphia, Pa., W. B. Sanders, 1996; 7: 148–154.
18. Knight et al., *Cancer Chemotherapy and Pharmacology* (in press).
19. Eastman et al., *Human Gene Therapy* 1997; 8: 313–322.
20. Eastman et al., *Human Gene Therapy* 1998; 9: 43–52.
21. Eastman et al., *Human Gene Therapy* 1997; 8: 765–773.
22. Scheule et al., *Human Gene Therapy* 1997; 8: 689–707.
23. Templeton et al., *Nature Biotechnology* 1997; 15: 647–652.
24. Gerson et al., *Biochemistry* 1993; 32: 7143–7151.
25. Sternberg et al., *FEBS Letters* 1994; 356: 361–366.
26. Sternberg et al., *Biochim Biophys Acta* 1998; 1375: 23–35.
27. Gustafsson et al., *Biochim Biophys Acta* 1995; 1235: 305–312.
28. Koltover et al., *Science* 1998; 281: 78–81.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A liposomal aerosol composition with protection against nebulizer-induced loss of cell transfection activity comprising:

(a) a plasmid DNA containing a gene;

(b) a cationic lipid;

(c) a neutral co-lipid; and (d) tryptone.

2. The liposome aerosol composition of claim 1, wherein said cationic and neutral co-lipids are selected from the group consisting of egg yolk phosphatidylcholine, hydrogenated soybean phosphatidylcholine, dimyristoylphosphatidylcholine, dilauroylphosphatidylcholine, dioleoylphosphatidylcholine, bis (guanidinium)-tren-cholesterol, dipalmitoyl phosphatidylcholine and dioleoylphosphatidylethanolamine.

3. The liposome aerosol composition of claim 1, wherein said tryptone is found in said composition in a concentration of from about 0.01% to about 5%.

4. A nebulized bis(guanidinium)-tren-cholesterol: dioleoylphosphatidylethanolamine liposome-DNA suspension useful for lipid-DNA transfections, wherein said liposome-DNA suspension resists degradation associated with nebulization and maintains stability and transfection efficiency after nebulization.

5. The nebulized liposome:DNA suspension of claim 4, wherein said bis(guanidinium)-tren-cholesterol is contained in said suspension in a concentration of from about 50 $\mu$g/ml to about 1,500 $\mu$g/ml.

6. The nebulized liposome:DNA suspension of claim 4, wherein said DNA is contained in said suspension in a concentration of from about 1 $\mu$g/ml to about 1000 $\mu$g/ml.

7. The nebulized liposome:DNA suspension of claim 4, wherein said bis(guanidinium)-tren-cholesterol and dioleoylphosphatidylethanolamine co-lipid are present in a ratio of from about 1:1 to about 1:4.

8. The nebulized liposome:DNA suspension of claim 4, wherein the ratio of DNA concentration to combined bis (guanidinium)-tren-cholesterol and dioleoylphosphatidylethanolamine concentration is about 1:1 to about 1:10.

9. The nebulized liposome:DNA suspension of claim 8, wherein the ratio of DNA concentration to combined bis (guanidinium)-tren-cholesterol and dioleoylphosphatidylethanolamine concentration is about 1:3 to about 1:5.

* * * * *

UNITED STATES PATENT AND TRADEMARK OFFICE

CERTIFICATE OF CORRECTION

PATENT NO. : 6,375,980 B1
DATED : April 23, 2002
INVENTOR(S) : Charles A. Densmore Jr. et al.

It is certified that error appears in the above-identified patent and that said Letters Patent is hereby corrected as shown below:

Column 1,
Line 59, please delete the space in “i s”.

Column 2,
Line 55, “shows” should read -- show --.
Line 59, “were” should read -- was --.

Column 3,
Line 37, “shows” should read -- show --.

Column 4,
Line 63, “shows” should read -- show --.

Column 5,
Line 10, “shows” should read -- show --.

Column 15,
Line 30, “form” should read -- from --.

Signed and Sealed this

Fourth Day of February, 2003

JAMES E. ROGAN
*Director of the United States Patent and Trademark Office*